(12) United States Patent
Serdarevic

(10) Patent No.: US 11,766,354 B2
(45) Date of Patent: Sep. 26, 2023

(54) DEVICES AND METHODS FOR NOVEL RETINAL IRRADIANCE DISTRIBUTION MODIFICATION TO IMPROVE AND RESTORE VISION WITHOUT PRODUCING CORNEAL VITRIFICATION

(71) Applicant: Aperture in Motion, LLC, Phoenix, AZ (US)

(72) Inventor: Olivia N. Serdarevic, Goshen, NY (US)

(73) Assignee: Aperture in Motion, LLC, Phoenix, AZ (US)

( * ) Notice: Subject to any disclaimer, the term of this patent is extended or adjusted under 35 U.S.C. 154(b) by 267 days.

(21) Appl. No.: 17/071,106

(22) Filed: Oct. 15, 2020

(65) Prior Publication Data

US 2021/0038425 A1 Feb. 11, 2021

Related U.S. Application Data

(60) Continuation of application No. 16/593,269, filed on Oct. 4, 2019, now Pat. No. 10,835,417, which is a
(Continued)

(51) Int. Cl.
*A61F 9/007* (2006.01)
*A61F 2/16* (2006.01)
*A61F 9/008* (2006.01)

(52) U.S. Cl.
CPC ............ *A61F 9/007* (2013.01); *A61F 2/1627* (2013.01); *A61F 2/1637* (2013.01);
(Continued)

(58) Field of Classification Search
CPC .. A61F 9/008; A61F 9/00842; A61F 9/00853; A61F 9/00863; A61F 9/00872; A61F 9/013; A61F 2/1637
See application file for complete search history.

(56) References Cited

U.S. PATENT DOCUMENTS 6,387,088 B1    5/2002   Shattuck et al.
9,526,656 B2   12/2016   Serdarevic et al.
(Continued)

FOREIGN PATENT DOCUMENTS

WO      2017046358 A1    3/2017

OTHER PUBLICATIONS

Alio et al., "Phakic Intraocular lens Implantation for Treatment of Anisometripia and Amblyopia in Chidren; 5-year Follow Up," Slack Incorporated, Feb. 1, 2011 (9 pages).
(Continued)

*Primary Examiner* — William H Matthews
(74) *Attorney, Agent, or Firm* — Duane Morris LLP

(57) ABSTRACT

Devices and methods for novel retinal irradiance distribution modification (IDM) to improve, stabilize or restore vision are described herein. Also encompassed herein are devices and methods to reduce vision loss from diseases, injuries and disorders that involve damaged and/or dysfunctional and/or sensorily deprived retinal cells. Conditions that may be treated using devices and methods described herein include macular degeneration, diabetic retinopathy and glaucoma. Therapy provided by retinal IDM devices and methods described herein may also be used in combination with other therapies including, but not limited to, pharmacological, retinal laser, gene and stem cell therapies.

12 Claims, 31 Drawing Sheets

Related U.S. Application Data division of application No. 15/693,208, filed on Aug. 31, 2017, now abandoned.

(52) U.S. Cl.
CPC .......... *A61F 2/1648* (2013.01); *A61F 2/1654* (2013.01); *A61F 9/008* (2013.01); *A61F 9/0079* (2013.01); *A61F 2009/00842* (2013.01); *A61F 2009/00853* (2013.01); *A61F 2009/00863* (2013.01); *A61F 2009/00872* (2013.01)

(56) References Cited

U.S. PATENT DOCUMENTS

| | | | |
|---|---|---|---|
| 9,532,904 | B2 | 1/2017 | Serdarevic et al. |
| 9,545,339 | B2 | 1/2017 | Serdarevic et al. |
| 10,835,417 | B2 | 11/2020 | Serdarevic |
| 2002/0038134 | A1 | 3/2002 | Greenberg et al. |
| 2011/0306919 | A1 | 12/2011 | Latina et al. |
| 2015/0133901 | A1 | 5/2015 | Serdarevic et al. |
| 2015/0297342 | A1* | 10/2015 | Rosen ............... A61F 2/1637 623/6.31 |
| 2017/0007395 | A1 | 1/2017 | Peyman |
| 2019/0046357 | A1 | 2/2019 | Knox et al. |
| 2019/0271849 | A1 | 9/2019 | Serdarevic et al. |
| 2020/0030082 | A1 | 1/2020 | Serdarevic |
| 2020/0197223 | A1 | 6/2020 | Yu et al. |

OTHER PUBLICATIONS

International Search report dated Jan. 7, 2019, in PCT/US1848910 (10 pages).

Alio et al., "Phakic Intraocular Lens Implantation for Treatment of Anisometripia and Amblyopia in Children; 5-year Follow Up," Slack Incorporated, Feb. 1, 2011 (9 pages).

International Search Report and Written Opinion dated Jan. 7, 2019, in PCT/US2018/048910 (10 pages).

International Search Report and Written Opinion dated Apr. 13, 2021, in PCT/US2020/064620 (12 pages).

* cited by examiner

DEVICES AND METHODS FOR NOVEL RETINAL IRRADIANCE DISTRIBUTION MODIFICATION TO IMPROVE AND RESTORE VISION WITHOUT PRODUCING CORNEAL VITRIFICATION

CROSS-REFERENCE TO RELATED APPLICATION

This application is a continuation of, and claims the benefit of priority to, U.S. application Ser. No. 16/593,269, which is a divisional of, and claims the benefit of priority to, U.S. application Ser. No. 15/693,208, filed Aug. 31, 2017. The disclosures of these applications are expressly incorporated herein by reference in their entireties.

FIELD OF THE INVENTION

The present invention relates to devices and methods for novel retinal irradiance distribution modification (IDM) to improve, stabilize or restore vision. The present invention also relates to devices and methods to reduce vision loss from diseases, injuries and disorders that involve damaged and/or dysfunctional and/or sensorily deprived retinal cells. The applications of the present invention include, but are not limited to, treatment of macular degeneration, diabetic retinopathy and glaucoma. The therapy provided by retinal IDM devices and methods of the present invention can also be used in combination with other therapies including, but not limited to, pharmacological, retinal laser, gene and stem cell therapies.

BACKGROUND

Conventional devices and methods offer suboptimal solutions for improving vision and/or restoring vision to reduce vision loss from diseases, injuries and disorders that involve damaged and/or dysfunctional and/or sensorily deprived retinal cells. Vision loss is caused by diseases, injuries and disorders including, but not limited to, age-related macular degeneration (AMD), Stargardt disease, Best vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, glaucoma or other neuroretinal or ganglion cell disorders and amblyopia (caused by refractive error, medial opacity or obstruction, or an oculomotor condition, or any combination thereof). AMD, DR and other retinal diseases and disorders are major causes of worldwide vision impairment, including blindness. There are great unmet needs for solutions that provide meaningful vision and vision-related quality of life improvements to patients who suffer from vision loss caused by retinal problems. Conventional devices and methods only offer suboptimal amelioration of, or compensation for, some symptoms of vision loss from such diseases, injuries and disorders.

Conventional devices and methods for amelioration of, or compensation for, symptoms of vision loss, such as telescopes (handheld, in electronic devices, in spectacles, in contact lenses, in intraocular lenses, or in the cornea) or annular multifocal corneal laser treatments, only magnify images within a small area of view. Devices and methods for amelioration of, or compensation for, symptoms of vision loss using prisms or prismatic effects (in spectacles, in contact lenses, or in intraocular lenses) only deviate images from objects within the visual field angularly onto a small area of the retina. The handheld and electronic telescopes require patients to remain stationary and these telescopes magnify a very small area of the patient's visual field. Telescopes in spectacles, contact lenses and intraocular devices require visual training over periods of weeks to months, produce tunnel vision, prevent binocular vision, and result in poor ambulatory vision. Telescopes or prisms in intraocular devices involve surgery with risks of severe intraoperative and postoperative complications and adverse events. Oculomotor training for eccentric fixation requires training over a period of weeks to months with diminishing effects over time and abnormal head positioning, with minimal improvements in reading speed and with minimal or no improvements in visual acuity. Prisms in glasses, contact lenses or intraocular lenses are poorly tolerated and can cause double vision. All optical devices on glasses or contact lenses fail to maintain a constant moment-to-moment visual correction as the eyes move, preventing the full effects of neural adaptation to develop. Retinal prostheses, such as eyeglass-mounted cameras that transmit wirelessly to a microelectrode array implanted intraocularly within or on a patient's retina cannot provide high resolution vision and provide only vague motion detection and shape discernment. Intraocular implants with telescopes, prisms, or microelectrode arrays involve surgery with risks of severe intraoperative and postoperative complications and adverse events, including death, loss of the eye, and complete loss of sight.

Conventional vision aids provide amelioration of, or compensation for, symptoms of visual loss but do not provide restorative benefits including, but not limited to, repair of damaged retinal cells or improvement of functioning of retinal cells.

Conventional drug therapies including, but not limited to, anti-vascular endothelial growth factor (anti-VEGF) agents for neovascular AMD, diabetic macular edema, and other neovascular retinal disorders and the prostaglandin analogs for glaucoma prevent further progression of vision loss but do not provide significant vision restoration for most patients. Conventional device therapies including, but not limited to, retinal laser photocoagulation, photodynamic laser therapy, radiation therapy, photobiomodulation, subthreshold micropulse laser therapy, glaucoma laser therapy and glaucoma surgery with or without shunt implantation do not improve vision significantly. Patients who suffer from dry AMD, marked by retinal dysfunction with drusen formation and eventual retinal atrophy, have no effective treatment options other than lifestyle modification, the use of glasses to block ultraviolet or blue light over the entire visual field, and the use of vitamins and other supplements.

SUMMARY OF THE INVENTION

The invention described herein includes IDM devices and methods to optically modify permanently, temporarily or with variable modifications over time in at least three retinal regions, including a retinal fixation region, spatial, temporal, spatiotemporal, chromatic, achromatic and contrast information distributions of environmental light from an ocular field of view by means of simultaneous light redirections from a retinal fixation region to at least two other spatially separated retinal regions (hereinafter: "IDM devices and methods"). The devices and methods of the invention described herein produce novel retinal irradiance distribution modifications (IDMs) to improve vision. The invention described herein also provides vision improvements, vision stabilization and/or vision restoration benefits to patients who have visual symptoms from, or have suffered visual loss from, diseases, injuries and disorders including, but not limited to, eyes with damaged and/or dysfunctional and/or sensorily deprived retinal cells. The invention described herein includes, but is not limited to, retinal IDM devices and methods for vision improvement and/or vision restoration to overcome vision loss caused by diseases, injuries and disorders including, but not limited to, age-related macular degeneration (AMD), Stargardt disease, Best's vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, nutritional retinal disorders, glaucoma or other neuroretinal or ganglion cell disorders and amblyopia (caused by refractive error, medial opacity or obstruction, or an oculomotor condition, or any combination thereof). In contrast to conventional devices and methods, the retinal IDM invention provides, without requiring oculomotor or perceptual training, better vision and/or quality of life outcomes, fewer and less severe complications or adverse effects, and greater patient convenience and comfort to patients treated with retinal IDM.

Embodiments of retinal IDM devices described herein include, but are not limited to, retinal IDM devices to produce cornea photovitrification (CPV); retinal IDM lasers and other light emitting sources to produce photoablation, photodisruption, photoionization, photochemical and/or photothermal keratoplasty; retinal IDM corneal crosslinking devices; retinal IDM radiofrequency transmitting devices; retinal IDM contact lenses; retinal IDM spectacles; retinal IDM corneal inlays; and retinal IDM intraocular lenses, all of which are configured to produce retinal IDM for vision improvement, with or without vision restorative benefits including, but not limited to, retinal cell repair and/or retinal regeneration.

In some embodiments of the present invention, retinal IDM devices and methods are combined with non-retinal IDM therapies including, but not limited to, pharmacological agents, including but not limited to, vascular endothelial growth factor antagonists, retinal laser, ionizing radiation, photobiomodulation, stem cell, genetic, epigenetic and optogenetic therapies.

While the description herein shows, describes, and points out novel features as applied to various embodiments, it will be understood that various omissions, substitutions, and changes in the form and details of the device or method illustrated can be made without departing from the spirit of the disclosure. As will be recognized, certain embodiments of the inventions described herein can be embodied within a form that does not provide all of the features and benefits set forth herein, as some features can be used or practiced separately from others. All changes which come within the meaning and range of equivalency of the claims are to be embraced within their scope.

DETAILED DESCRIPTION OF THE INVENTION

Figure 1:
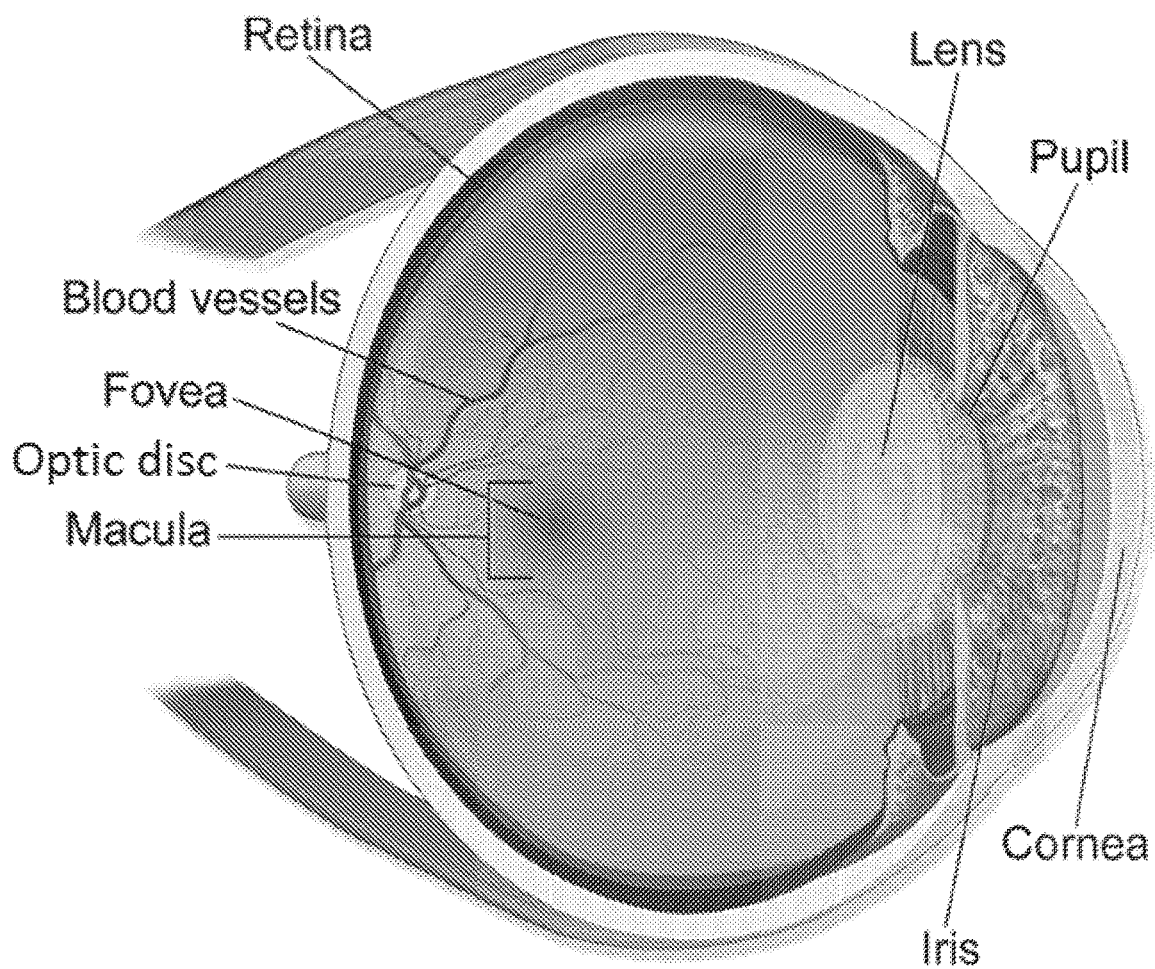
FIG. 1 is a cutaway drawing of an eye showing principal ocular structures.

The retinal irradiance distribution modification (IDM) invention described herein includes retinal IDM devices and methods that optically modify permanently, temporarily or with variable modifications over time in at least three retinal regions, including a retinal fixation region, spatial, temporal, spatiotemporal, chromatic, achromatic and contrast information distributions of environmental light from an ocular field of view by means of simultaneous light redirections from a retinal fixation region to at least two other spatially separated retinal regions (hereinafter: "IDM"). Retinal IDM devices and methods have applications for vision improvement or stabilization and/or vision restoration and/or amelioration of and/or compensation for visual symptoms from ophthalmic conditions, diseases, injuries and disorders, including, but not limited to, in eyes with visual loss due to diseases, injuries and disorders that involve damaged and/or dysfunctional and/or sensorily deprived retinal cells. The IDM devices and methods reduce visual loss caused by diseases, injuries and disorders including, but not limited to, age-related macular degeneration (AMD), Stargardt disease, Best vitelliform macular dystrophy, light-induced retinal injuries, cone dystrophies, reverse retinitis pigmentosa, myopic macular degeneration, macular scars, diabetic retinopathy (DR), macular edema, macular hole, macular detachment, macular pucker, vascular retinal disorders (including but not limited to retinal vein occlusions and Coats' Disease), retinitis pigmentosa, nutritional retinal disorders, glaucoma or other neuroretinal or ganglion cell disorders and amblyopia (caused by refractive error, medial opacity or obstruction, or an oculomotor condition, or any combination thereof).

Vision processing involves the interaction of the two eyes and the brain through a network of neurons, receptors, and other specialized cells. The first steps in this sensory process include the stimulation of light receptors in the retina, conversion of the light stimuli into neural signals, processing of these neural signals through many kinds of retinal interneurons, and transmission of electrical signals containing spatial, temporal, spatiotemporal and chromatic visual information from each eye to the brain. Processing by retinal interneurons involves chemical and electrical messages sent among retinal cell types including the feedforward pathway from photoreceptors to bipolar cells and on to ganglion cells, along with interactions of these cell types with and among horizontal and amacrine cells. This information is further processed in the brain. Functional vision results when the brain integrates retinal information across space, time, and saccades.

Retinal irradiance is the amount of light power per unit area that is incident on the retina. Irradiance is measured in units of $W/m^2$ where W is the light power in watts and m is a meter of length. An eye with a retinal disorder can have decreased retinal sensitivities of varying magnitudes to light irradiance in retinal regions. Decreased retinal sensitivities can be demonstrated by diagnostic testing, including, but not limited to, microperimetry. There is incorrect and/or impartial visual processing of light rays within the environmental field of view of a retinal region with decreased retinal sensitivities. Following retinal IDM treatment by retinal IDM devices and methods of the invention described herein, the distribution of visual information in the environmental field of view of an eye is modified by multiple and spatially separated redirections of the light rays onto multiple retinal regions, including regions with better retinal sensitivities. Retinal IDM, therefore, is distinct from a modification of the total irradiance onto the entire retina and may or may not include a modification of the total irradiance onto the entire retina. Retinal spectral irradiance is the amount of light power per unit area per unit wavelength that is incident on the retina. Detection of light by the retina is different for different wavelengths of light and for photopic, mesopic and scotopic illumination conditions. IDM devices and methods are useful in all illumination conditions including, but not limited to, day vision and night vision illumination conditions. Unless otherwise noted in this application, retinal irradiance is always considered for visible light with a spectral distribution including, but not limited to, sunlight or light with a color rendering index (CRI) similar to sunlight (i.e., CRI≥80, with a maximum of 100—a perfect match of the spectral distribution to sunlight) and for photopic illumination conditions including, but not limited to, daylight.

It is understood that retinal irradiance and retinal irradiance distribution can be measured for both model and ex vivo eyes by using photometric instrumentation known to one skilled in the art including, but not limited to, photodiode arrays, charge-coupled device (CCD) sensors and complementary metal oxide semiconductor (CMOS) sensors. It is also understood to one skilled in the art that retinal irradiance and retinal irradiance distribution can be predicted using raytracing computations with model eyes.

The retinal irradiance distribution, together with its spatiotemporal, chromatic, achromatic and contrast information, can be specified on various spatial and temporal scales. Spatial scales include, but are not limited to: A) receptive fields of domains of retinal cells including, but not limited to, spatial scales as small as an individual photoreceptor and including both the center and surround of each cell's receptive field; B) the entire fovea; C) the entire macula; D) the entire central visual field that extends to an eccentricity of ca. 20°; and E) the entire visual field. Locations on the retina with respect to the center of the foveola can be specified in terms of polar coordinates $r,\theta$ or $r',\theta$ in which r is the distance in mm units or r' is the distance in terms of retinal eccentricity in units of degrees, and $\theta$ is the angular coordinate.

Temporal scales include, but are not limited to: A) a moment-to-moment timescale that can be as short as 10 milliseconds, during which irradiance and contrast can be modified from: i) changes in the radiance of objects in visual space, ii) from movements of the eye, including both fixational movements and saccades that cause light (from different objects in the visual space) to irradiate a spatial region of the retina, or iii) any combination of i and ii; B) an intermediate timescale, that extends to several minutes duration, during which processes of retinal adaptation occur; C) a long timescale, that is in the range of days to years duration, during which the overall irradiance on a spatial region of the retina can affect the health of retinal cells; and D) a second long timescale that be in the range of days to years duration, during which processes of neural adaptation occur.

Contrast refers to changes in irradiance across the spatial and temporal scales described above. Contrast can also refer to changes in irradiance on temporal scales that match the dynamics of the light responses in retinal cells. Contrast can also refer to changes in irradiance on spatio-temporal scales that match the dynamics of motion-sensitive cells in the retina. Contrast can also refer to changes in spectral irradiance that match the chromatic sensitivities of retinal cells.

Figure 2:
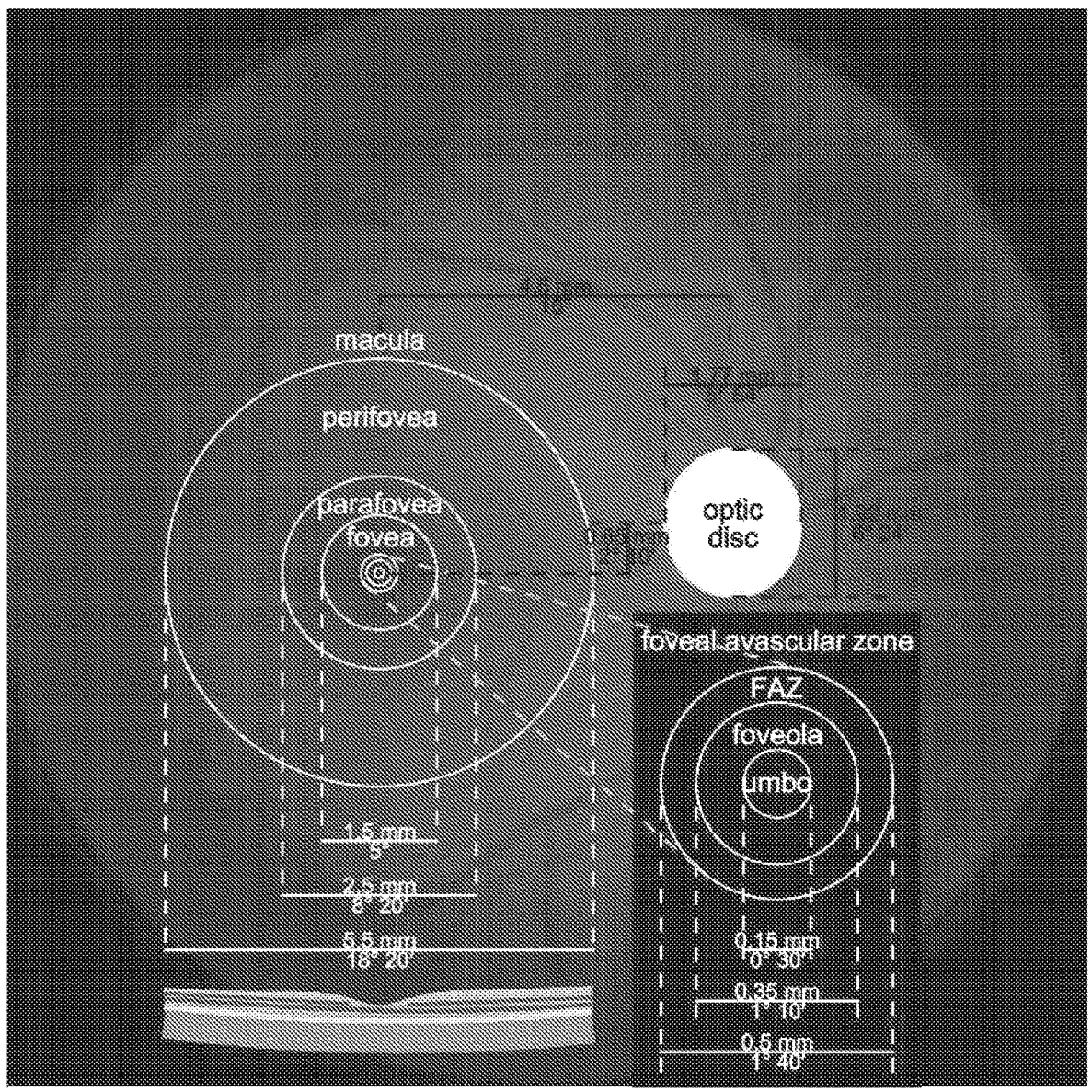
FIG. 2 is a drawing of an eye in the vicinity of the macula showing retinal structures and dimensions.
Figure 3:
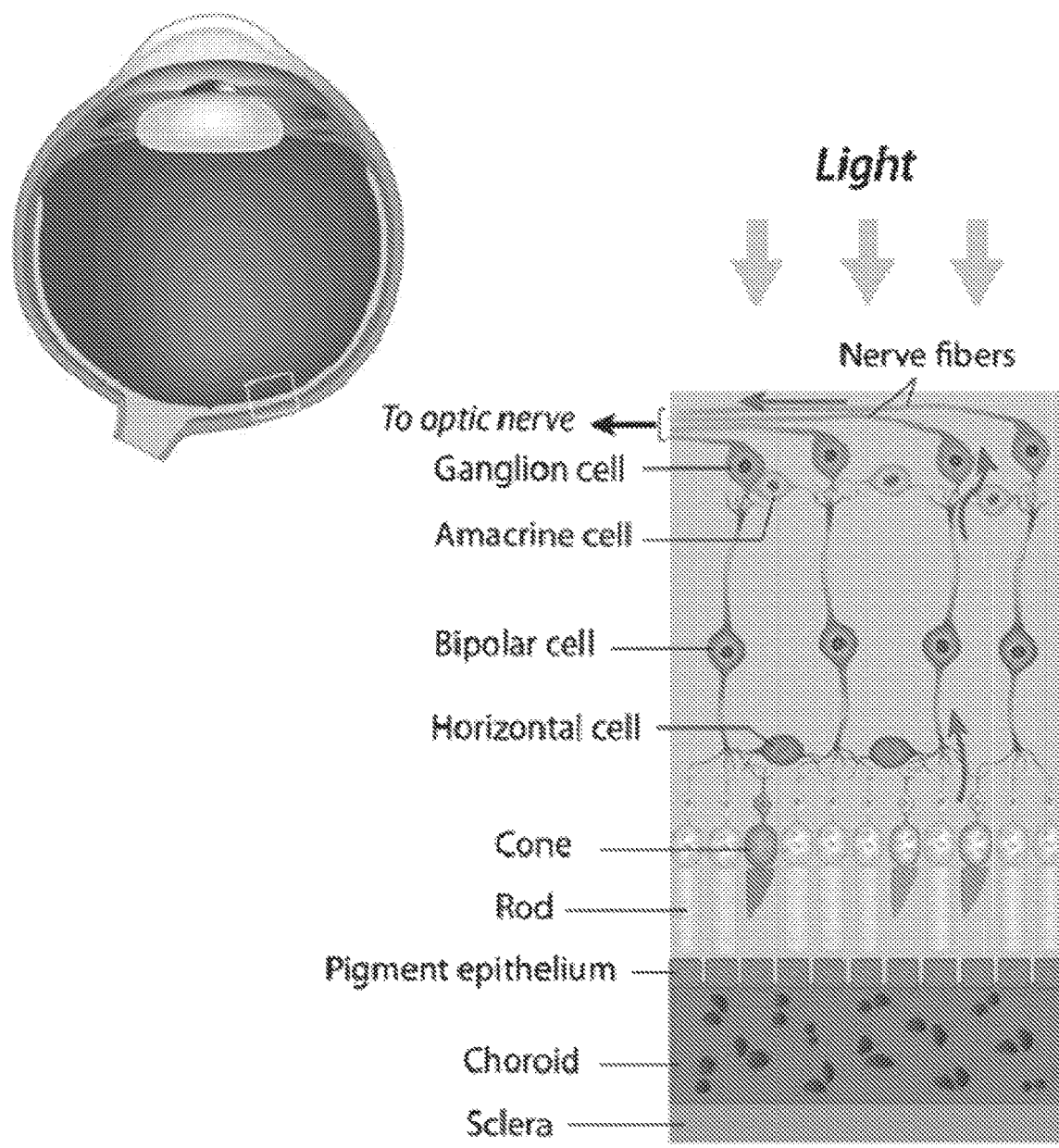
FIG. 3 is a schematic retinal microstructure and vision transduction drawing.

The retina of the eye is illustrated on the cutaway drawing of an eye shown in FIG. 1. Principal ocular structures are the cornea, the iris (defining the pupil aperture), the lens and the retina including the fovea, macula, optic disc and blood vessels. The region of the retina in the vicinity of the macula is shown in FIG. 2, with identification of the fovea and other retinal areas together with their dimensions. A retinal schematic microstructure and vision transduction drawing is shown in FIG. 3, in which light produced by IDM devices and methods irradiates the retinal, producing electrical signals from photoreceptor (cone and rod) cells; these electrical signals are pre-processed by specialized retinal (horizontal, bipolar, amacrine and ganglion) cells leading to action potentials (electrical "spikes") that propagate through the optic nerve (and ultimately to the visual cortex) through axons (nerve fibers) emanating from retinal ganglion cells. The choroid contains capillary blood vessels that provide nutrients to retinal cells and that transport waste products from the retina.

Figure 4:
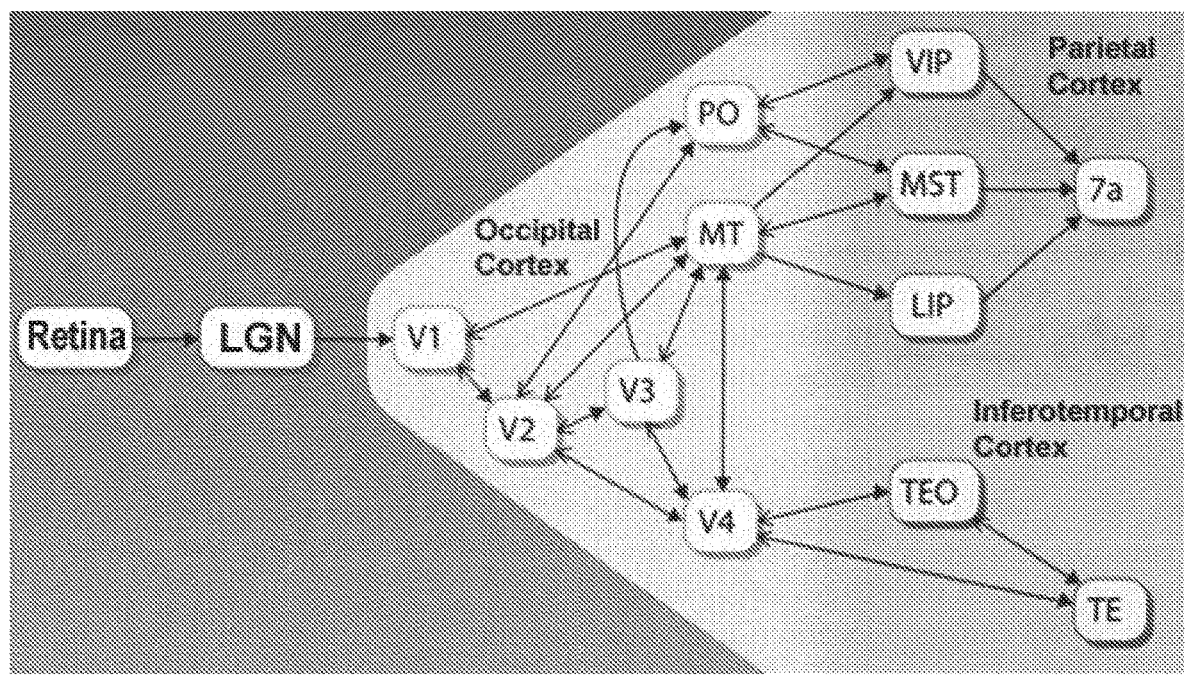
FIG. 4 is a schematic simplified visual pathways drawing.

FIG. 4 shows schematic simplified pathways for the cortical processing of visual information. Retinal ganglion cell axons connect to the lateral geniculate nucleus (LGN) as well as to other subcortical structures including, but not limited to, the superior colliculus that are not shown. LGN relay cells connect to the primary visual cortex (area V1). The primary visual cortex in turn connects to multiple cortical visual areas (including, but not limited to, the ventral stream and the dorsal stream) that process information to provide visual outcomes including, but not limited to, spatial vision, motion perception, depth perception, form perception and color vision. The visual cortex interacts with the thalamus via recurrent loops to produce integrated visual perception. Visual cortical areas also interact with subcortical structures including, but not limited to, the basal ganglia, thalamus, cerebellum, superior colliculus and brainstem to control eye movements. Subcortical visual processing includes, but is not limited to, eye and head movements, pupil sizes and circadian rhythm. It is understood that vision improvement including, but not limited to, neuroadaptation involves the complex interaction of neural processing between and among all the stages of the visual pathway.

Figure 5:
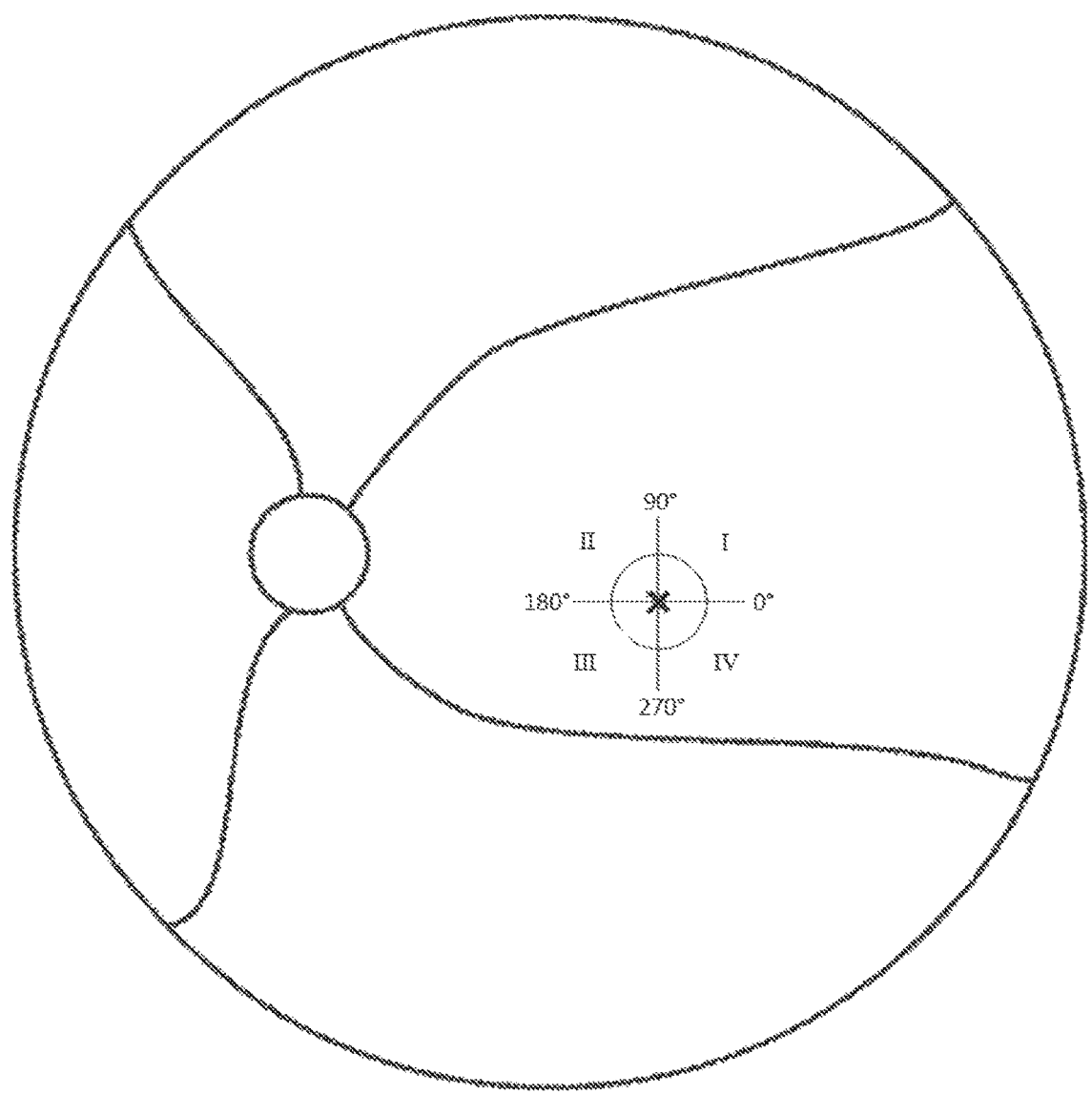
FIG. 5 is a schematic retina drawing showing the fovea (right circle), optic disc (left circle) and retinal vessels (wavy lines extending to the optic disc).

A schematic retina drawing is shown in FIG. 5. The fovea is shown as the circle at the right in FIG. 5 with 0°-180° (temporal-nasal) and 90°-270° (superior-inferior) meridians dividing the retinal area into four quadrants: I (superior-temporal), II (superior-nasal), III (inferior-nasal) and IV (inferior-temporal). Foveal polar coordinates r,θ specify locations on the retina referenced to the foveolar center "X". The fovea is approximately 0.75 mm (2.5° eccentricity) in radius; it contains the highest density of photoreceptors (cones) for the highest spatial resolution of vision. The optic disc is shown as the circle at the left in FIG. 3 with retinal blood vessels represented as wavy lines.

Figure 6:
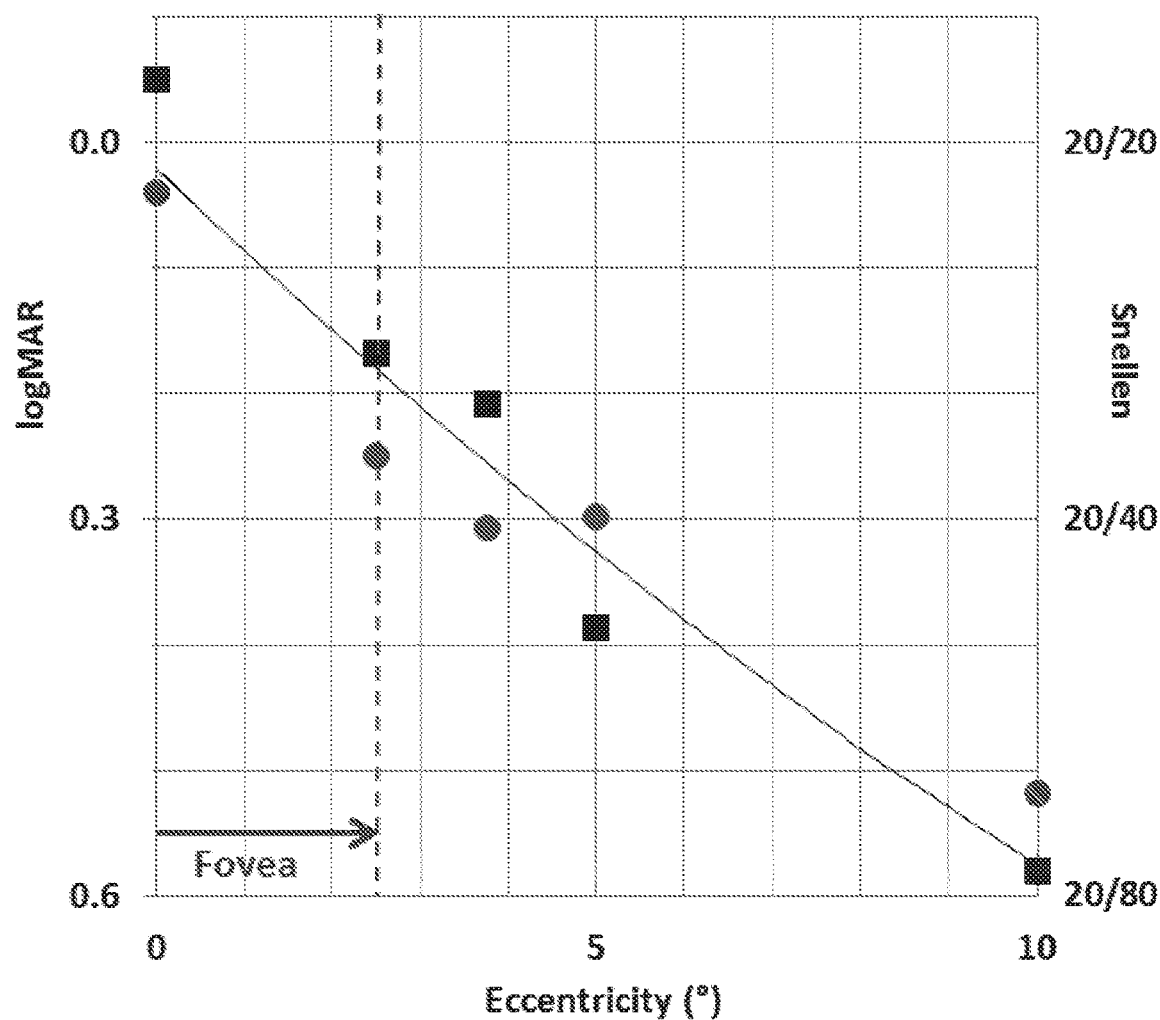
FIG. 6 is a graph of visual acuity vs. retinal eccentricity using the foveolar center as the zero-eccentricity reference.

FIG. 6 shows the variation of visual acuity (both in logMAR and Snellen units) as a function of retinal eccentricity. FIG. 6 is redrawn from FIG. 3 of Williams D R and Coletta N J, Cone spacing and the visual resolution limit, J Am Opt Soc A (1987). Measurements are for two subjects (circle and square symbols); a mean value of 0.907 logMAR (20/162 Snellen) was also measured at 20° retinal eccentricity. A quadratic fit to the measurements is shown. Conversion from retinal eccentricity: 1° retinal eccentricity=approximately 0.3 mm. The fovea extends to ca. 2.5° retinal eccentricity. The greatest visual acuity is obtained for light focused onto the foveal center of a fully functional retina. Both defocus and lack of full retinal functionality can reduce visual acuity. Conventional vision aids including, but not limited to, spectacles and contact lenses can improve focus but cannot improve retinal functionality. Although useful vision can be based on using large regions of the retina outside the fovea (i.e., outside approximately 2.5° retinal eccentricity)—see FIG. 6—these regions outside the fovea may be underutilized if higher spatial resolution visual information from the fovea is weighted preferentially in the visual cortex.

The retinal irradiance distribution modification (IDM) invention described herein includes retinal IDM devices and methods that optically modify permanently, temporarily or with variable modifications over time in at least three retinal regions, including the fovea or another retinal fixation region, spatial, temporal, spatiotemporal, chromatic, achromatic and contrast information distributions of environmental light from an ocular field of view by means of light redirections from the fovea or another retinal fixation region to at least two other spatially separated retinal regions. The retinal regions are defined by ranges of polar coordinates, wherein the spatially separated retinal regions are non-overlapping regions, partly overlapping regions or any combination of non-overlapping and partly overlapping regions and wherein the amount(s) and location(s) of retinal IDM are for predetermined spatial distribution(s) with or without predetermined temporal distributions. The retinal irradiance distribution modifications contain information including, but not limited to, spatial, temporal, spatiotemporal, chromatic, achromatic and contrast information or any combination thereof.

The retinal IDM invention has applications for both vision improvement and vision restoration in diseased eyes as described herein: A—for vision and quality of life improvement and B—for vision restoration benefits including, but not limited to, retinal cell repair and/or retinal regeneration. It is understood that, in some embodiments, vision improvement can be obtained by retinal IDM treatment using the retinal IDM devices and methods described herein without vision restoration benefits, in that some regions of the retina may remain partly or completely dysfunctional or may even become less functional as time elapses after retinal IDM treatment. It is also understood that, in some other embodiments, both vision improvement and beneficial vision restoration effects, including increased functionality of some regions of the retina that were partly or completely dysfunctional prior to retinal IDM treatment, can be obtained due to retinal IDM treatment.

In some embodiments of the invention described herein that are intended for vision improvement, retinal IDM devices and methods are configured to optically redirect light from one or more partly or completely dysfunctional retinal areas and to redirect that light, in whole or in part, onto two or more retinal areas, including one or more functional retinal areas, wherein the dysfunctional retinal areas include, but are not limited to, at least one of an area of dysfunctional foveal photoreceptors, multiple areas of dysfunctional foveal photoreceptors, a dysfunctional preferred retinal locus (PRL), multiple dysfunctional PRLs, multiple spatially separated dysfunctional retinal areas of photoreceptors or any combination thereof, wherein the functional retinal areas include, but are not limited to, at least one of a retinal area of functional photoreceptors, multiple retinal areas of functional photoreceptors, and multiple spatially separated functional retinal areas of photoreceptors wherein all the functional retinal areas of photoreceptors have functional signaling to functional ganglion cells.

In some embodiments of the invention described herein, the functional retinal areas include, but are not limited to, a. at least two spatially separated areas in at least two different quadrants (see FIG. 5) and b. at least one spatially separated area in each of the four retinal quadrants (see FIG. 5).

The retinal areas are defined by ranges of polar coordinates, wherein the spatially separated retinal areas are non-overlapping areas, partly overlapping areas or any combination of non-overlapping and partly overlapping areas, wherein the amount(s) and location(s) of retinal IDM are for predetermined spatial distribution(s) with or without predetermined temporal distribution(s), and wherein the retinal irradiance distribution modifications contain information including, but not limited to, spatial, temporal, spatiotemporal, chromatic, achromatic and contrast information or any combination thereof.

In some embodiments of the retinal IDM invention described herein, the spatially separated retinal areas include multiple areas in each of the four retinal quadrants in order to increase the likelihood of redirecting light: a. onto a functional area or areas in eyes with many dysfunctional areas, b. onto multiple functional areas to be used for different visual tasks, and c. onto multiple functional areas that can be used if or as the retinal disease progresses.

In some embodiments of the retinal IDM devices and methods of the invention described herein, the retinal IDM alters the moment-to-moment patterns of light irradiance coming from edges and objects to increase the relative irradiance difference on nearby photoreceptors (i.e., increases the contrast).

In some embodiments of the retinal IDM devices and methods of the invention described herein, the pattern of retinal irradiance distribution modification (IDM): (i) improves neural computation with integration of additional and/or more correctly coded retinal information from macular and peripheral retinal cells—including, but not limited to, photoreceptors, bipolar cells, amacrine cells, horizontal cells, Müller glial cells, ganglion cells or any combination of retinal cells—to enable processing of more complete stimulus patterns and/or (ii) improves functioning of retinal circuitry, including connectivity functions in visual processing involving photoreceptors, ganglion cells, amacrine cells, bipolar cells, horizontal cells, and Müller cells or any combination thereof and/or (iii) triggers processes of neural adaptation, including but not limited to, use of alternate, latent, and/or new visual pathways in the retina and brain including, but not limited to: a. rerouting of visual information encoded by peripheral areas of the retina to neurons at high levels of the visual cortex with receptive fields normally tasked with encoding objects at the center-of-gaze, permitting beneficial alteration of crowding properties with reduced critical spacing in those peripheral areas and/or b. changing the destination of saccadic eye movements (herein, referred to as a "fixation") to new retinal loci and/or c. beneficially changing the amplitude and/or speed of eye movements within a fixation and/or d. beneficially changing the interaction of the saccadic corollary discharge circuit with the rest of the visual cortex and/or e. producing more effective and spontaneous searching to achieve more effective integration of a greater amount of more correct visual information by searching mechanisms including, but not limited to, spontaneously producing motor learning in the eye movement strategy to both collect information from a greater area of the visual scene and use more functional retinal cells for improved visual information.

In some embodiments of the retinal IDM devices and methods of the invention described herein, retinal IDM re-routes central visual information (typically, but not limited to, information at the center-of-gaze) through alternative retinal pathways, thereby restoring the transmission of high-resolution spatial information from these areas of visual space to the rest of the brain—including but not limited to the cerebral cortex, basal ganglia, thalamus, superior colliculus, and other brainstem nuclei—thereby enhancing global visual processing mechanisms, including, but not limited to: a. enhancing global pooling of contour information and/or b. improving shape discrimination and/or c. improving motion processing and/or d. improving color processing and/or e. improving visually guided behavior or any combination thereof.

In some embodiments of the retinal IDM devices and methods of the invention described herein, retinal IDM triggers processes of neural adaptation in central brain circuits (including, but not limited to, the visual cortex and/or the visual thalamus and/or superior colliculus or any combination thereof), including but not limited to structural and synaptic plasticity that include, but are not limited to:
a. restoring visual perception to areas of visual space corresponding to damaged areas of the retina, which had, prior to treatment, produced little or no visual perception (i.e., were scotomata) by inducing neurons in central brain circuits to develop spatial receptive fields covering these previously scotomata; and/or
b. reducing and/or eliminating distortions of the visual field in the areas of visual space around the scotomata by incorporating these new spatial receptive fields into local spatial maps and by reorganizing them into a continuous, undistorted map of visual space (i.e., counteracting inaccurate perceptual filling-in).

In some embodiments of the retinal IDM devices and methods of the invention, retinal IDM improvement of visual perception occurs by the formation of new visual pathways from functional areas of the retina that encode high fidelity information about regions of visual space, which were, prior to treatment, within scotomata. For example, the distortion of the visual field perceived by patients with macular degeneration can result from an incorrect remapping of the spatial receptive fields of neurons in the central brain. In this remapping, the receptive fields of neurons covering the dysfunctional region of the retina expand and shift to include areas of visual space corresponding to functional regions of the retina. This causes neurons farther away to remap in a similar fashion, and so on. Taken together, these processes induce a global distortion in the receptive field map, with the clinical symptom of straight line objects such as letters, telephone poles and signs becoming wavy, also known as metamorphopsia. After treatment by some embodiments of the IDM invention, the newly formed receptive fields covering areas of visual space that were, prior to treatment, within scotomata become incorporated into the spatial map within each visual area. This incorporation induces a process of reorganization that reverses the distortion caused by the macular degeneration and thereby restores a continuous, undistorted map of visual space within each visual area. The wavy letters, poles and signs become straight again.

In some embodiments of the retinal IDM devices and methods of the invention described herein, retinal IDM enables beneficial cortical reorganization including, but not limited to, altered crowding properties with smaller critical spacing in the retinal periphery, wherein retinal IDM directs attention to new eccentric preferred loci or other retinal viewing area/s. The altered crowding properties include, but are not limited to, a loss of the radial-tangential anisotropy of the crowding zone. Retinal IDM permits, after spontaneous repeated use of the new preferred retinal location ("PRL") and/or PRLs and/or retinal viewing areas, decreases in the sizes of the crowding zones around the new PRL or PRLs or retinal viewing areas because of cortical plasticity. The plasticity causes the spatial properties at the PRL/PRLs/retinal viewing areas to become more fovea-like. Both the magnitude and extent of crowding are decreased to the amounts normally found around the fovea. Reduction in the extent of crowding along the major axis contributes to the less elliptical shape of the crowding zone at the PRL/PRLs/retinal viewing areas, which decreases the detrimental effects of crowding, thereby improving visual acuity and visual function.

Some embodiments of the retinal IDM devices and methods of the invention described herein, unlike conventional devices and methods, improve vision by y awakening, without requiring oculomotor or perceptual training, residual functional vision pathways, thereby enabling patients to discover and use the resulting vision immediately or within days or within weeks and with additional improvement over months.

In some embodiments of the retinal IDM devices and methods of the invention described herein, vision improvement is greatly enhanced by having a pattern of retinal IDM that is stable across time on a moment-to-moment basis as the eyes move naturally in vision.

Some embodiments of the retinal IDM invention described herein produce, without requiring perceptual or oculomotor training, natural awareness in a treatment subject of one or more alternate functional visual pathways and natural sensorimotor learning without causing tunnel vision, polyopia or binocular diplopia in a treated subject.

Some embodiments of the retinal IDM devices and methods of the invention described herein stabilize vision and/or reduce, compared to an untreated control group, the rate of vision loss and/or improve vision after a vision loss from a disease, injury or disorder involving retinal cell damage, retinal cell dysfunction, retinal cell sensory deprivation or any combination thereof. The vision improvement includes, but is not limited to, visual acuity (including both uncorrected and best spectacle-corrected visual acuity for distance, intermediate and near visual acuity), hyperacuity, stereoacuity, vernier acuity, contrast sensitivity, depth of focus, color vision, peripheral vision, night vision, face recognition, light adaptation, dark adaptation, vision-related quality of life, or any combination thereof.

In some embodiments of the retinal IDM devices and methods of the invention described herein, retinal IDM enables sustained and/or transient attention. When spatial covert attention is directed to a target location, sustained attention enhances sensitivity strictly via contrast gain, whereas transient attention involves a mixture of both contrast gain and response gain.

In some embodiments of the retinal IDM devices and methods of the invention described herein, retinal IDM improves visual functioning, including, but not limited to, connectivity functions in visual processing of retinal tertiary network cells, including, but not limited to, ganglion cells, amacrine cells, bipolar cells, Müller cells or any combination thereof.

In some embodiments of the retinal IDM devices and methods of the invention described herein, retinal IDM improves visual field deficits on perimetry and/or microperimetry examination and/or preferential hyperacuity perimetry and/or restores electroretinogram (ERG) amplitudes and/or visually evoked potentials.

Some embodiments of the retinal IDM devices and methods of the invention described herein enable preferred retinal locus or loci relocation to more functional location or locations on an ongoing basis and for different binocular visual tasks.

Some embodiments of the retinal IDM devices and methods of the invention described herein, unlike conventional devices and methods: (i) enable unilateral or bilateral treatment of patients with visual loss from disorders damaging retinal cells and/or decreasing functioning of retinal cells and/or sensorily depriving retinal cells and/or (ii) provide rapid vision improvement continuing over months and years with additional sensory and/or oculomotor neuroadaptation without requiring perceptual or oculomotor control training.

Some embodiments of the retinal IDM devices and methods of the invention described herein, unlike conventional devices and methods with life-threatening or sight-threatening complications or adverse events, provide vision improvement after loss from retinal disorders without complications or adverse events including, but not limited to, clinically significant changes in intraocular pressure, central corneal thickness, corneal endothelial cell density; corneal decompensation, corneal epithelial cell loss, infection or loss of visual functions including, but not limited to, best-corrected distance visual acuity, best-corrected near visual acuity, contrast sensitivity, and stereopsis.

In some embodiments of the invention described herein that are intended for vision restoration effects including, but not limited to, retinal cell repair and/or retinal regeneration, retinal IDM devices and methods are configured to:

a. decrease by at least 0.1% the retinal irradiance from the field of view on spatially separated retinal areas, including partially or completely dysfunctional retinal areas, wherein the decrease continues over the defined long time scale, and increase by at least 0.1% the retinal irradiance from the field of view on spatially separated (other than those in a.) retinal areas, including more functional retinal areas, wherein the increase continues over the defined long timescale wherein it is understood that retinal irradiance and retinal irradiance distribution can be measured for both model and ex vivo eyes by using photometric instrumentation known to one skilled in the art including, but not limited to, photodiode arrays, charge-coupled device (CCD) sensors and complementary metal oxide semiconductor (CMOS) sensors.

Some embodiments of the retinal IDM devices and methods of the invention described herein improve vision, after loss from disorders damaging retinal cells and/or decreasing functioning of retinal cells and/or sensorily depriving retinal cells, with a single and rapid treatment that is comfortable and pain-free, does not require medication after treatment, and does not require retreatment. By comparison, conventional devices and methods have numerous disadvantages and treatment burdens including, but not limited to, at least one of the following: inconvenience for patients, requirement that the patient remain stationary for usage, limitation to the use of only one eye or only one eye at a time, limitation to treatment only in one eye (or, if the method can be performed in two eyes, only sequential treatment), requirement for a long and/or painful procedure, requirement of post-procedure medications, requirement for constant uncomfortable or difficult insertion, provocation of retinal inflammation, and requirement for multiple/repeat procedures.

Some embodiments of the devices and methods of the retinal IDM invention described herein repair and/or restore retinal cells and/or increase retinal cell functioning and/or decrease progressive damage to retinal cells in addition to significantly improving vision with rapid improvement of neurocomputation and beneficial neuroadaptation continuing long-term (i.e., over a period of time extending from days through years after treatment).

Some embodiments of the devices and methods of the retinal IDM invention described herein compensate for deterioration of the retina caused by photoreceptor or other retinal cell damage with or without repair of retinal cells and/or triggering visual system repair processes, including but not limited to, beneficial modulation of trophic factors and biological repair processes. Biological repair processes include, but are not limited to, regrowth of photoreceptor outer segments, reprogramming of Müller cells, regeneration of retinal cells, and reduction of drusen volume in subjects with diseased photoreceptors, retinal pigment epithelial cells and/or Bruch's membrane.

Some embodiments of the retinal IDM devices and methods of the invention described herein repair and/or restore retinal cells and/or increase retinal cell functioning with fewer adverse effects and more patient convenience. The devices and methods of the present invention overcome drawbacks and deficiencies of the prior art, including conventional devices and methods for repairing retinal cells or increasing retinal cell function or decreasing progressive retinal cell damage by targeting different mechanisms with the novel retinal IDM to produce better treatment outcomes more comfortably and more conveniently with fewer systemic and ocular adverse effects. In some embodiments of the invention described herein, retinal IDM not only improves vision by altering neurocomputation and neuroadaptation but also by repairing and/or restoring retinal cells. In some embodiments of the invention, retinal IDM also triggers visual system repair processes, including biological repair processes, including, but not limited to, regrowth of photoreceptor outer segments, reprogramming of Müller cells, regeneration of retinal cells and reduction of drusen volume, wherein the retinal IDM a. decreases by at least 0.1% retinal irradiance from the field of view of spatially separated retinal areas within at least one of a foveal area, another PRL, multiple PRLs, a non-PRL retinal area, multiple non-PRL retinal areas or any combination thereof, wherein the decrease continues over the previously defined long timescale, wherein the reduced retinal irradiance decreases deleterious processes including, but not limited to, photo-oxidative stress, metabolic stress or a combination thereof within viable retinal cells, wherein reduction of such deleterious processes includes, but is not limited to, sparing photoreceptors, slowing progression of photoreceptor loss, decreasing drusen volume or any combination thereof; and b. increases by at least 0.1% retinal irradiance from the field of view on retinal areas (other than in a.), including on areas with viable retinal cells, wherein the increase continues over the previously defined long timescale, wherein the increased retinal irradiance increases activation by the viable cells of at least one of cell repair, cell regeneration, or a combination thereof within at least one of damaged retinal cells or retinal areas with non-functional cells; and c. redirects spatial, temporal, spatiotemporal, chromatic, achromatic and contrast information contained in irradiance distributions from one or more dysfunctional to one or more functional areas of the retina.

In some embodiments of the invention described herein, retinal IDM improves retinal sensitivity, wherein the improved retinal sensitivity includes, but is not limited to, improved sensitivity of viable cone photoreceptors, viable rod photoreceptors, viable ganglion cells, amacrine cells, viable bipolar cells and/or partially or completely regenerated retinal cells. It is understood that retinal sensitivity can be measured by one skilled in the art by using diagnostic instrumentation including, but not limited to, microperimetry instrumentation. In some embodiments of the invention described herein, retinal IDM produces in a treated eye with a retinal disorder, including, but not limited to, macular degeneration, over a time period of months or years at least one of the following: a. an increase in retinal sensitivity in a retinal region, b. a decrease in the rate of retinal sensitivity loss compared to an untreated control group, c. a decrease in the rate of photoreceptor loss compared to an untreated control group, d. a decrease in the area of photoreceptor loss, e. a decrease in drusen volume, f a regeneration of retinal cells, or g. any combination thereof.

In some embodiments of the invention described herein, retinal IDM increases retinal absorption of photons in some retinal areas to improve visual processing for vision and retinal image quality while decreasing cumulative photoabsorption and photodamage in other retinal areas, including, but not limited to, the foveal area, other fixation areas, other macular areas, peripheral areas and any combination of retinal areas in which cumulative photoabsorption and photodamage should be reduced.

In some embodiments of the invention described herein, retinal IDM selectively decreases light irradiance including, but not limited to, on the fovea, on other fixation areas (preferred retinal loci), on other macular areas, on peripheral retinal areas, and on any combination of retinal areas to selectively decrease oxidative stress and/or phototoxicity to retinal structures including, but not limited to, photoreceptors, retinal pigment epithelial cells, Bruch's membrane and choriocapillaris and/or selectively decreases cumulative light damage, by decreasing oxidative stress and/or phototoxicity including, but not limited to, in the fovea, in other fixation area/s (preferred retinal loci), in other macular areas, in peripheral retinal areas, or in any combination of retinal areas.

In some embodiments of the invention described herein, retinal IDM provides beneficial effects including, but not limited to, selective prevention of photoreceptor loss, selective reduction of the rate of progression of photoreceptor loss, and decrease of photoreceptor loss including, but not limited to, apoptosis and/or necrosis and/or pyroptosis and/or autophagy.

In some embodiments of the invention described herein, retinal IDM selectively reduces light-induced oxidative stress and reactive oxygen species in the retinal areas where irradiance is decreased in order to produce beneficial effects including, but not limited to, protection of photoreceptor DNA, promotion of DNA repair, decrease of pathophysiological parainflammation, decrease of inflammasome activation, decrease of detrimental autophagy, including but not limited to, chaperone-mediated autophagy (a.k.a. microautophagy), decrease retinal cellular death via apoptosis, decrease activation of proinflammatory and proangiogenic pathways, decrease other deleterious processes associated with oxidative stress and its resultant excessive reactive oxygen species.

In some embodiments of the invention described herein, retinal IDM selectively decreases photo-oxidation of the retinoid A2E in photoreceptor outer segments. In some embodiments of the invention, retinal IDM selectively decreases A2E formation and/or promotes A2E reduction in photoreceptor outer segments without the adverse ocular events related to delayed dark adaptation, such as nyctalopia, dyschromatopsia, blurred vision and photophobia, of current investigational drugs that reduce A2E formation.

In some embodiments of the invention described herein, retinal IDM selectively decreases retinal irradiance and/or cumulative retinal irradiance in retinal areas to decrease oxidative phosphorylation in retinal areas to decrease reactive oxygen species, thereby preventing mitochondrial dysfunction and/or reversing mitochondrial dysfunction. In some embodiments of the invention, retinal IDM reduces metabolic and/or oxidative stress and/or metabolic instability of retinal structures including, but not limited to, retinal cells (including, but not limited to, photoreceptors, retinal pigment cells, Müller glial cells, and ganglion cells) and Bruch's membrane in some retinal areas to produce beneficial effects including, but not limited to, reduction of damage to and/or repair of and/or regeneration of damaged retinal structures including, but not limited to, retinal cells (including, but not limited to, photoreceptors, retinal pigment cells, Müller glial cells, and ganglion cells) and Bruch's membrane in some retinal areas.

In some embodiments of the invention described herein, retinal IDM selectively decreases retinal irradiance and/or cumulative retinal irradiance in some retinal areas and/or decreases oxidative stress to produce beneficial effects including, but not limited to, harnessing Müller glial cells for photoreceptor cell protection and/or regeneration and/or increasing Müller glial cell transdifferentiation and/or decreasing Müller glial cell gliosis and/or preventing deleterious retinal remodeling and/or preserving glutamine synthetase expression in Müller cells and/or enabling the retinal microenvironment around Müller cells to support cone function.

In some embodiments of the retinal IDM invention described herein, retinal IDM selectively decreases retinal irradiance and/or cumulative retinal irradiance in some retinal areas, thereby causing reduction of drusen volume (i.e., the number and/or size of drusen).

In some embodiments of the invention described herein, retinal IDM selectively decreases retinal irradiance and/or cumulative retinal irradiance in some retinal areas to produce beneficial effects including, but not limited to, beneficial modulation of trophic factors and regeneration and/or rescue of retinal structures including, but not limited to, retinal cells (including, but not limited to, photoreceptors, retinal pigment epithelial cells, Müller glial cells, and ganglion cells) and Bruch's membrane and the external limiting membrane.

Embodiments of the invention described herein include retinal IDM devices and methods based on light sources (including, but not limited, to continuous wave and pulsed lasers, including, but not limited to, lasers for corneal photovitrification, corneal photodisruption, intralenticular photodisruption, corneal photoionization, corneal photodissociation, corneal photoablation, thermal keratoplasty, and photo-welding), corneal crosslinking systems, corneal radiofrequency transmitters, spectacles, contact lenses, corneal inlays, intraocular lenses for insertion in phakic, aphakic or pseudophakic eyes, and combinations thereof configured to produce retinal irradiance distribution patterns utilizing designs, materials, and optics for retinal IDM in many areas of the retina or throughout the retina to stabilize vision, improve vision, restore vision or reduce the rate of vision loss compared to an untreated control group after visual loss from disorders that involve damaged and/or dysfunctional and/or sensorily deprived retinal cells; wherein the retinal IDM devices and methods are configured to optically modify permanently, temporarily or with variable modifications over time in at least three retinal regions, including the fovea or another retinal fixation region, spatial, temporal, spatiotemporal, chromatic, achromatic and contrast information distributions of environmental light from an ocular field of view by means of simultaneous light redirections from the fovea or another retinal fixation region to at least two other spatially separated retinal regions, wherein the retinal regions are defined by ranges of polar coordinates, wherein the spatially separated retinal regions are non-overlapping regions, partly overlapping regions or any combination of non-overlapping and partly overlapping regions and wherein the amount(s) and location(s) of retinal IDM are for predetermined spatial distribution(s) with or without predetermined temporal distributions and wherein the retinal irradiance distribution modifications contain information including, but not limited to, spatial, temporal, spatiotemporal, chromatic, achromatic and contrast information or any combination thereof. In some embodiments of the retinal IDM devices and methods described herein, the retinal devices produce retinal IDM to simultaneously and optically redirect light from partly or completely dysfunctional retinal areas and to redirect that light, in whole or in part, onto one or more functional retinal areas, wherein the retinal irradiance distribution modifications contain information including, but not limited to, spatial, temporal, spatiotemporal, chromatic, achromatic and contrast information or any combination thereof. In some embodiments of the retinal IDM devices and methods described herein, the retinal devices produce retinal IDM wherein the amount and location of retinal IDM is for spatially separated retinal areas, that are non-overlapping areas, partly overlapping areas or any combination of non-overlapping and partly overlapping areas; the amount and location of such retinal IDM is for a predetermined spatial distribution with or without a predetermined temporal distribution; wherein the amount and location of retinal IDM has a pattern and symmetry distinct from that caused by self-generated image modifications including, but not limited to, i) eye movements that cause a single translation of the entire visual field on the retina, ii) lens accommodation that causes a change in the focus of the entire visual field on the retina and iii) pupil dilation/constriction that causes a rapid brightening/dimming of the entire visual field on the retina, as this prevents the central brain from being able to compensate for, and hence partially cancel, the effects of retinal IDM; wherein retinal IDM, without requiring oculomotor and/or perceptual training, inhibits at least one visual pathway used for fixation and excites at least one alternate functional visual pathway for fixation in an eye; wherein retinal IDM, without requiring oculomotor and/or perceptual training, produces awareness in a treatment subject of at least one or multiple alternate functional visual pathways; wherein retinal IDM also may produce beneficial effects including, but not limited to, reduction of damage to and/or repair of and/or regeneration of damaged retinal structures including, but not limited to, retinal cells (including, but not limited to, photoreceptors, retinal pigment cells, Müller glial cells, and ganglion cells) and Bruch's membrane in some retinal areas; and wherein retinal IDM improves vision after a vision loss from one or more of a disease, injury or disorder involving one or more of retinal cell damage, retinal cell dysfunction, retinal cell sensory deprivation or any combination thereof, wherein the improved vision is configured to result in improvement of vision-related outcomes including, but not limited to, visual acuity (including both uncorrected and best spectacle-corrected visual acuity for distance, intermediate and near visual acuity), hyperacuity, depth of focus, color vision, peripheral vision, contrast sensitivity, stereoacuity, vernier acuity, light adaptation, dark adaptation, vision-related quality of life, or any combination thereof.

Figure 7:
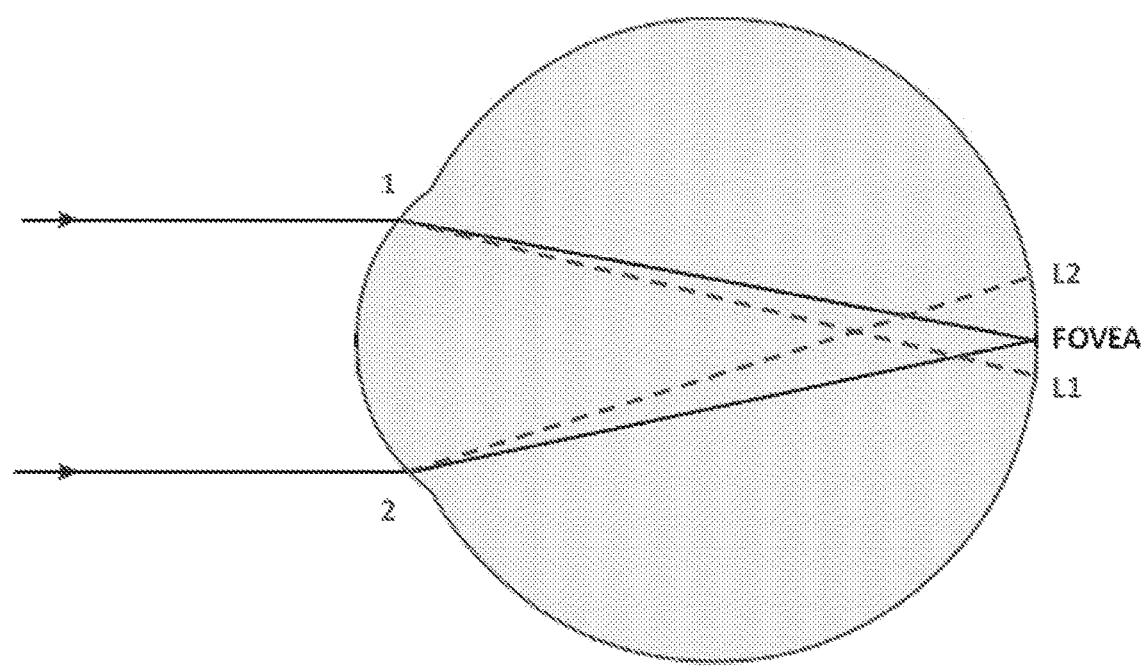
FIG. 7 is a schematic eye drawing with two light rays incident on the paracentral cornea at points 1 and 2.

Some embodiments of the retinal IDM invention described herein alter the cornea of the eye. In some corneal embodiments, a laser retinal IDM device is used to modify radii of curvature (ROCs) of the cornea as schematically shown in FIG. 7. In the unmodified cornea, rays of light incident on points 1 and 2 are focused onto the fovea, as shown by solid lines in FIG. 7. Decreasing the ROCs at points 1 and 2 (not shown in FIG. 7) changes the directions of light rays to irradiate locations L1 and L2 that are outside the fovea. In FIG. 7, the modified ROC at point 2 is decreased by a greater amount compared to the modified ROC at point 1, both of which are decreased relative to the unmodified radius of curvature; in this case, the greater decrease in radius of curvature at point 2 produces a larger redirection of the light ray to irradiate location L2 that is separated by a greater distance from the fovea than the light ray that irradiates location L1. The light ray relocations at any points on the cornea can be produced by corneal modifications including, but not limited to, modifications of corneal radii of curvature, corneal indices of refraction, corneal diffraction, corneal scattering and any combination of corneal modifications thereof. It is understood that the sample light rays shown in FIG. 7 are only representative of the entire set of light rays that are mapped from object space to image space(s) on the retina. In some embodiments of the invention described herein, retinal IDM includes light ray relocations produced by corneal modifications within two or more corneal regions including, but not limited to, central through paracentral sectors extending to 7 mm or larger optical zone with alternating steeper and flatter sectors within the full 360° angular range on the cornea.

Figure 8:
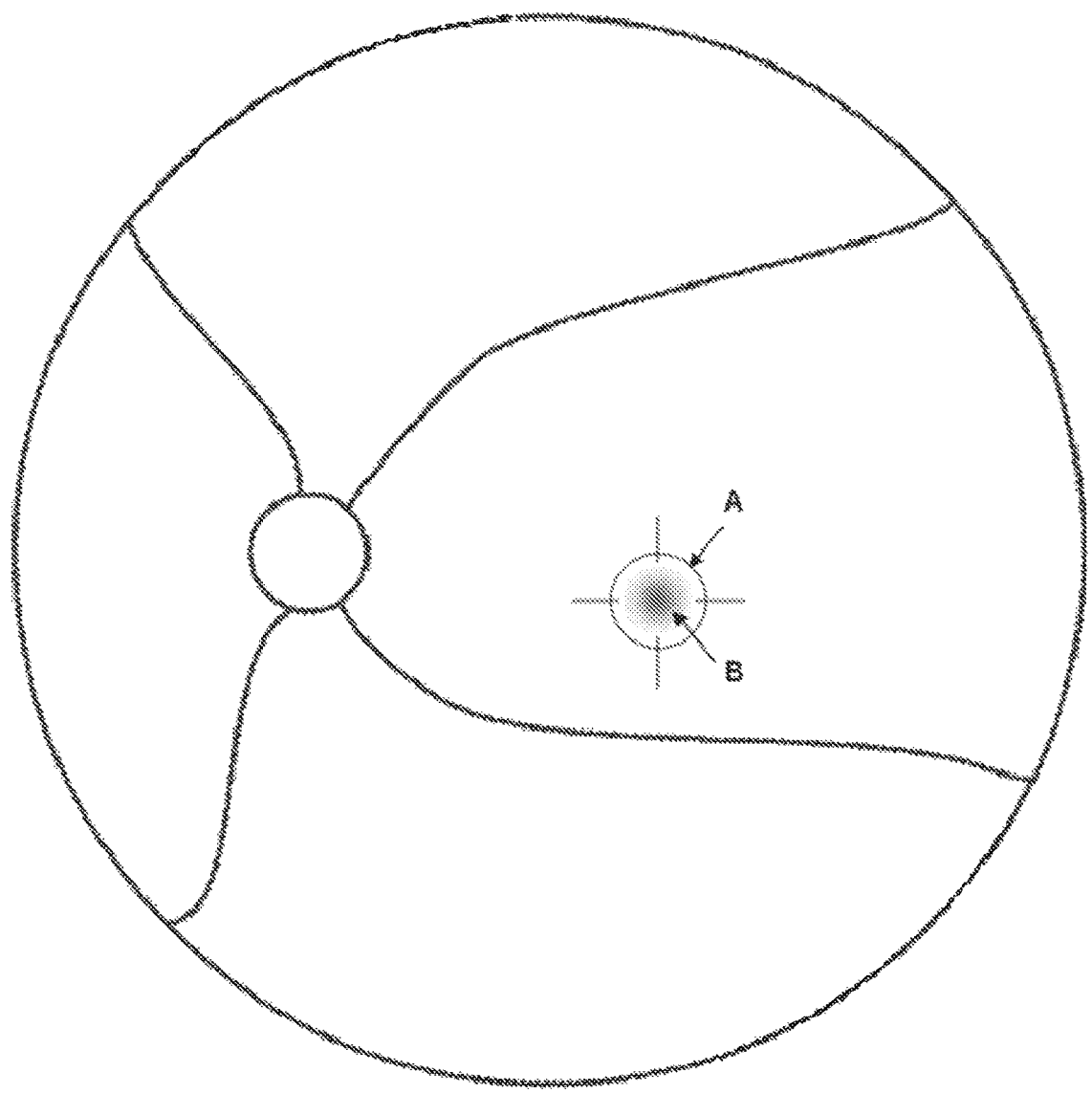
FIG. 8 is a schematic retina drawing showing the fovea A with a central dysfunctional retinal area B.
Figure 9:
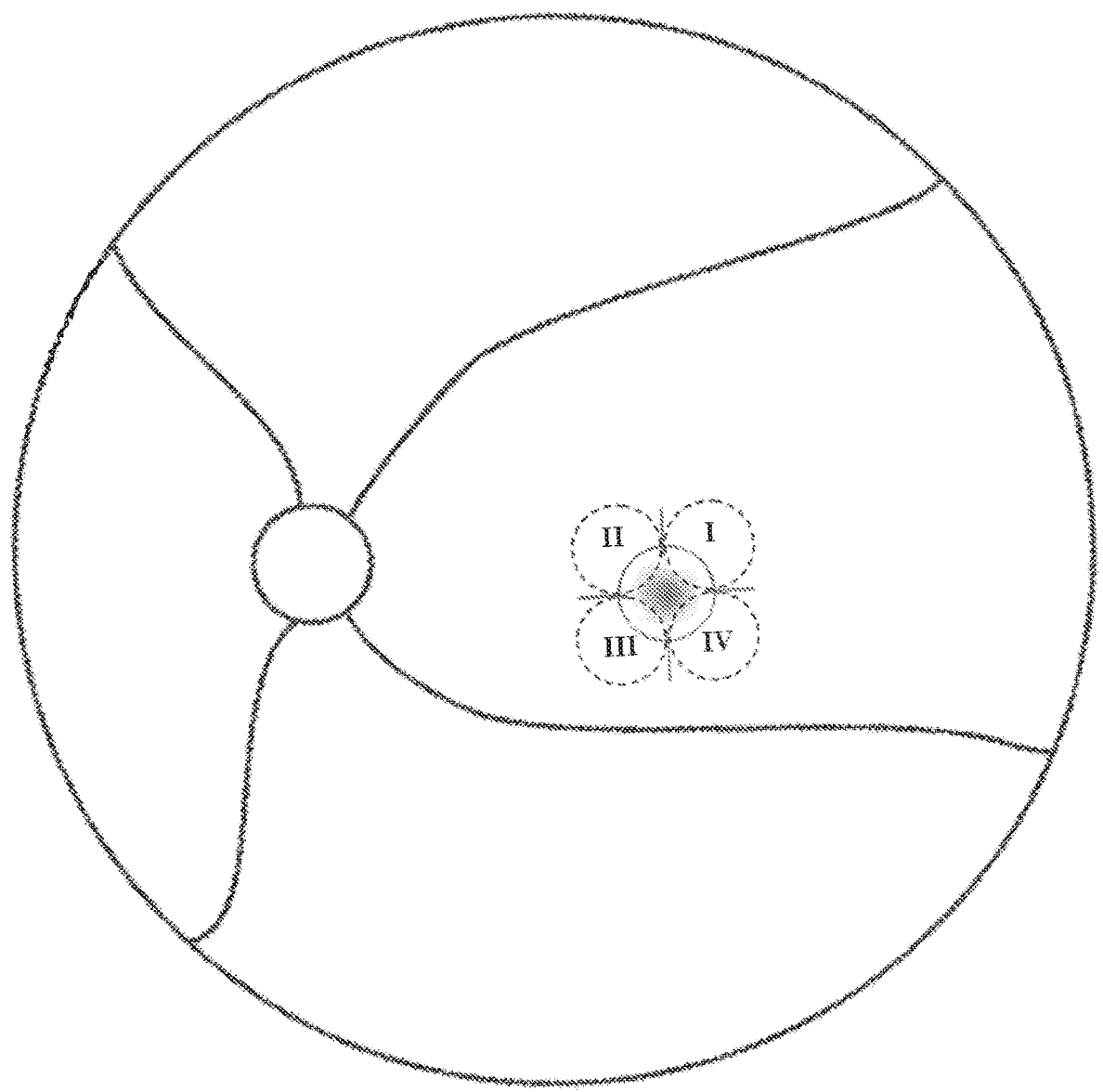
FIG. 9 is a schematic retina drawing showing a four-quadrant retinal irradiance distribution from a central area into quadrants I through IV.

FIG. 8 is a schematic retina drawing showing the fovea A with a central dysfunctional area B. In this case, a retinal IDM device including, but not limited to, a device that modifies the cornea should be designed to redirect light rays, with spatiotemporal, contrast, chromatic and achromatic information, away from the central dysfunctional area B to functional retinal areas including, but not limited to, the functional zone of the fovea outside area B. FIG. 9 is a schematic retina drawing that illustrates a four-quadrant retinal IDM that may be produced by using a retinal IDM device for retinal IDM from the central dysfunctional retinal area into four functional retinal areas.

Figure 10:
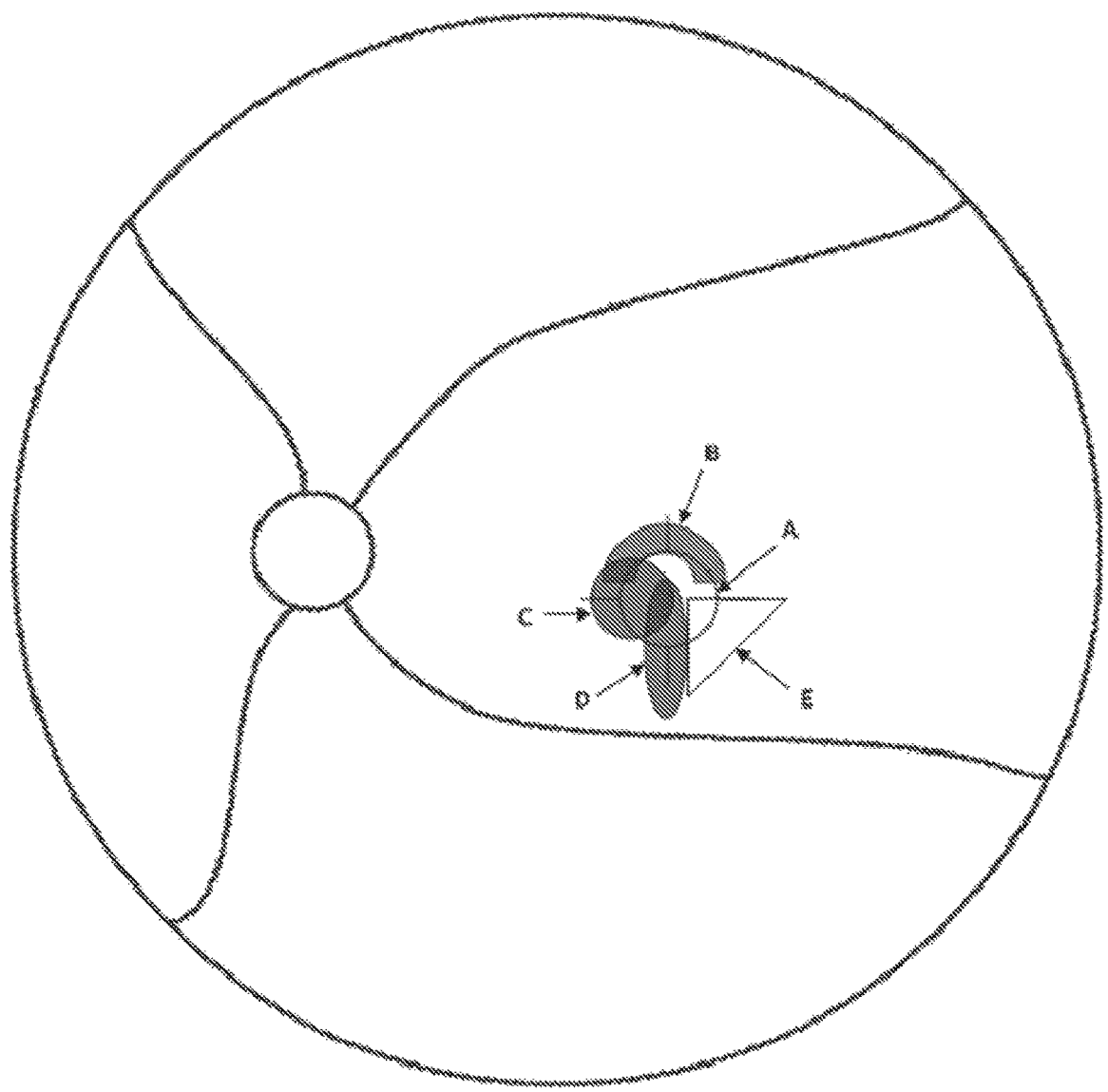
FIG. 10 is a schematic retina drawing showing the fovea A with non-central dysfunctional retinal areas B, C and D and a candidate functional retinal area E into which retinal IDM can increase retinal irradiance by directing irradiance away from B, C and D.

FIG. 10 shows dysfunctional and functional retinal areas with a variety of shapes and locations on the retina. It is understood by anyone skilled in the art that any retinal IDM device should be configured to produce retinal IDM away from dysfunctional retinal areas (B, C and D in the example of FIG. 10) and onto functional retinal areas; in the case of FIG. 10, the functional retinal area E is a candidate area into which retinal IDM can be used for vision and visual function improvements.

Preferred embodiments of retinal IDM devices and methods used to modify radii of curvature of the cornea include, but are not limited to, corneal photovitrification (CPV) IDM devices (hereinafter "CPV-IDM" devices) that use a light source to irradiate the cornea in order to produce photovitrification of at least one volume of corneal stromal material, as described in U.S. Pat. No. 9,526,656 by methods described in U.S. Pat. No. 9,532,904 both of which are incorporated herein in their entirety by reference. CPV-IDM treatment produces at least one volume of corneal stromal material that is modified in structure and properties from its naturally occurring condition into a non-naturally occurring glass-like condition as described in U.S. Pat. No. 9,545,339 which is incorporated herein in its entirety by reference. In the invention described herein, preferred retinal IDM devices and methods are used to treat one or more volumes of corneal stromal material with treatment patterns that extend retinal IDM into one or more functional regions of the retina. Several applications of the device and methods described in the above-referenced patents are also incorporated herein for devices and methods described herein in their entirety by reference. These applications include, but are not limited to, vision and visual function improvements, compensation for age-related focus dysfunction, reduction of myopia progression and reduction of axial length elongation progression.

Figure 11A:
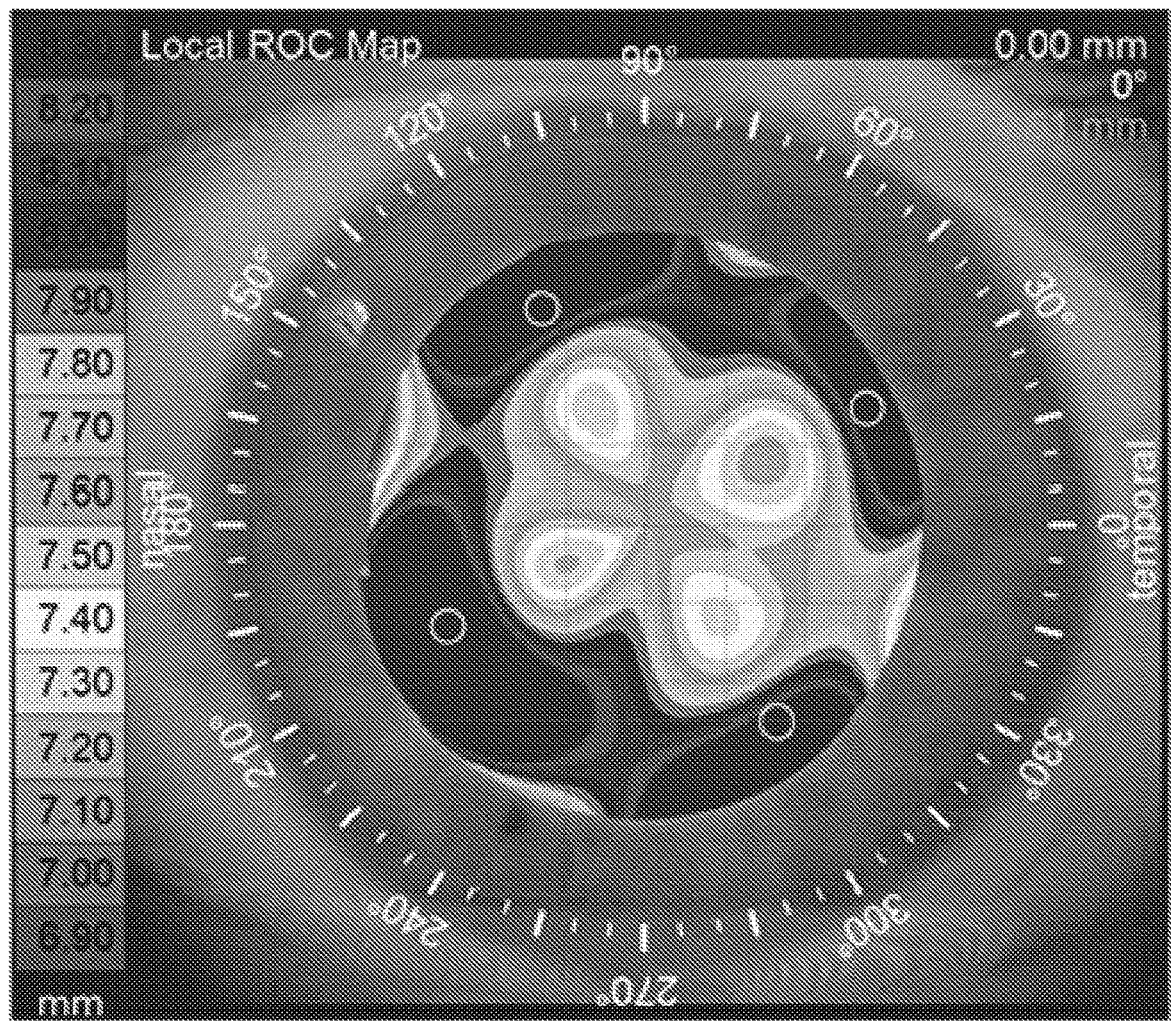
FIG. 11A is a corneal map showing local radii of curvature produced by CPV IDM treatment.
Figure 11B:
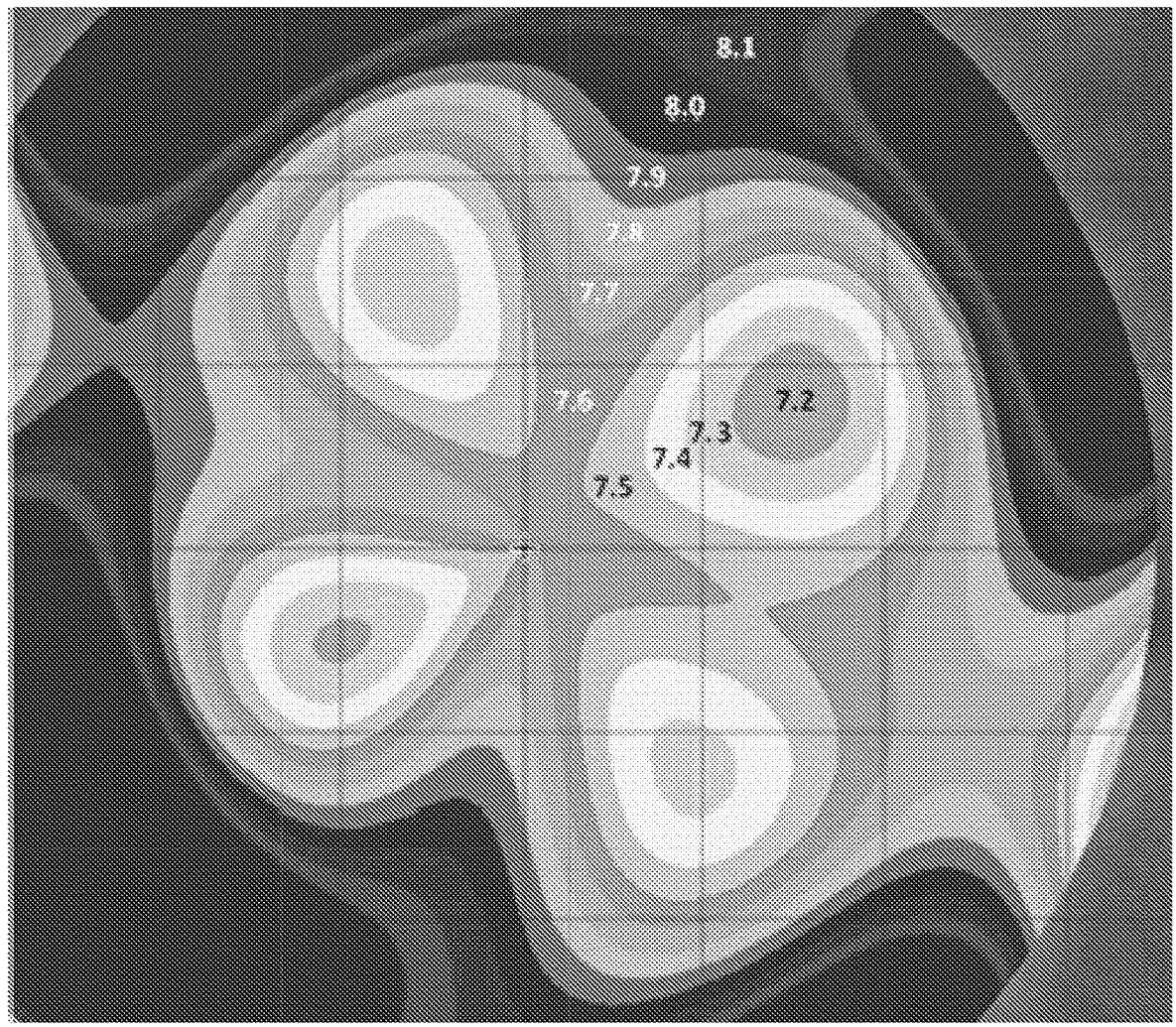
FIG. 11B shows an enlarged central area of FIG. 11A.
Figure 12:
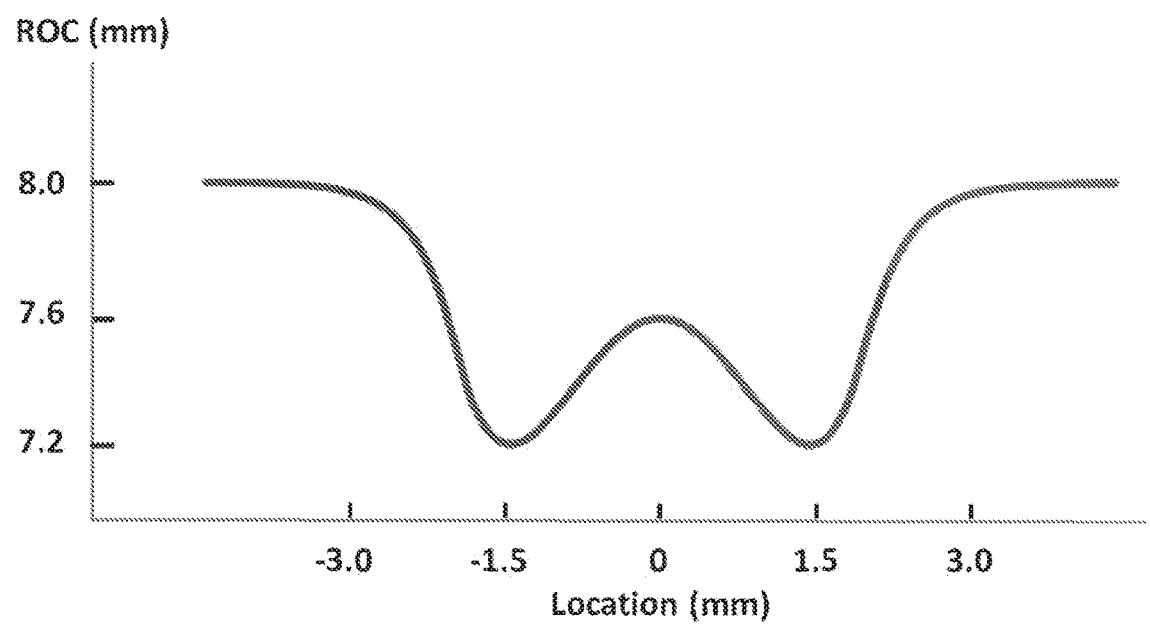
FIG. 12 shows a schematic corneal anterior surface radius of curvature (ROC) profile for retinal IDM.

One highly preferred embodiment of a retinal IDM device and method produced the treatment pattern of corneal radii of curvature (ROC) shown in FIG. 11A and the enlarged portion of FIG. 11A shown in FIG. 11B. FIG. 11B shows 0.1 mm incremental boundaries in radii of curvature; the actual ROCs vary continuously from one incremental boundary to another. FIG. 12 shows a continuous ROC profile that approximates the ROC profile along the 30°-210° meridian of the treatment pattern shown in FIG. 11A. The ROCs can be symmetric as shown in FIG. 12 or asymmetric with variable shapes. Locations of minimum ROCs can be centered or decentered with respect to the pupil centroid (or another centration reference). The untreated cornea had a ROC of approximately 7.6 mm in the central optical zone (within 3 mm diameter); the treated cornea had ROCs in the range of 7.2 to 7.8 mm within the same zone. The CPV-IDM treatment also produced significant ROC changes throughout the cornea, extending to the peripheral cornea at the 7 mm optical zone. The resultant CPV-IDM treatment change in FIG. 11A can be approximately described as four sets of alternating steeper/flatter sectors within the central (3 mm diameter) optical zone surrounded by four sets of flatter regions in the paracentral cornea between ca. 5 to 7 mm optical zone. The variations in ROCs produce redirection of light rays from four aspheric extended "lenslets" that redirect retinal irradiance onto functional retinal areas similar to those illustrated in FIG. 9, as well as redirection of light rays from other regions of the cornea. The ROC pattern shown in FIGS. 11A and 11B was produced by a retinal IDM device that caused CPV-IDM treatment of four small volumes of corneal stromal tissue located underneath the surface treatment areas shown as small white circles on FIG. 11A. Due to the biomechanical properties of the cornea, the highly localized treatments in four small volumes of corneal stromal tissue produced non-local effects that extended from each treated volume toward the corneal center with peak effects approximately midway between the treated volumes and the corneal center. CPV-IDM treatment produced non-local ROC changes over the entire cornea extending from the center of the cornea to at least the 7 mm optical zone.

In some preferred embodiments of the retinal IDM invention described herein, devices that use corneal photovitrification (CPV) for retinal IDM produce corneal modifications including, but not limited to, modifications of corneal radii of curvature, corneal indices of refraction, corneal diffraction, corneal scattering and any combination of corneal modifications thereof throughout the cornea using various patterns, including but not limited to four circular non-central volume treatments. In corneal radii of curvature modifications, CPV-IDM treatment induces various non-central locations and amplitudes of major depressions and/or elevations in the corneal anterior surface with resultant increases and/or decreases in anterior corneal radii of curvature throughout the cornea.

In some preferred embodiments of the invention described herein, CPV-IDM for retinal IDM produces changes in radii of curvature that alter the irradiance distribution in all four quadrants of the retina, wherein retinal IDM causes decreased or increased irradiance and/or contrast on retinal regions and/or microregions, wherein the changed ratios of light and dark edges of viewed objects change the irradiance contrast. In some embodiments, CPV-IDM patterns for retinal IDM of the present invention are centered on the pupil centroid (PC) or corneal vertex (CV) or coaxially sighted corneal light reflex (CSCLR). In some embodiments, CPV-IDM patterns for retinal IDM are decentered relative to the PC, CV or CSCLR.

In some preferred embodiments of the invention described herein, CPV-IDM for retinal IDM does not produce deleterious retinal effects including, but not limited to, retinal inflammation and retinal wound healing. In contrast to conventional devices and methods of retinal laser therapy (including, but not limited to, laser retinal photocoagulation, laser retinal photodynamic therapy and subthreshold micropulse diode laser therapy) and photobiomodulation therapy, CPV-IDM devices and methods do not use laser or light emitting diode (LED) light to irradiate the retina; CPV-IDM uses only natural environmental light to irradiate the retina and therefore is free from deleterious retinal effects associated with exposure of the retina to laser and other unnatural non-environmental light. In some preferred embodiments of CPV-IDM treatments for retinal IDM, only "eyesafe" light is used to irradiate the cornea; "eyesafe" light is completely absorbed by the cornea and other pre-retinal ocular structures, thereby preventing direct irradiation of the retina.

In some embodiments of the retinal IDM invention described herein, the CPV-IDM treatment for retinal IDM of the present invention continues to compensate for ongoing damage to or decreased functioning of retinal cells from the underlying disease process for months and years after the treatment of the present invention. In some embodiments, the ongoing neural compensation for ongoing damage to retinal cells or decreased functioning of retinal cells from the underlying disease process is facilitated by ongoing changes in the retinal IDM produced by methods of the present invention, which, for example, enable changes in corneal anterior surface depressions and/or elevations over days, weeks, months, or years. Some preferred embodiments of the invention, such as with some methods using corneal photovitrification to produce retinal IDM, produce increases and/or decreases in radii of curvature of the anterior cornea throughout the cornea, that change gradually over days, weeks, months, or years to continue to compensate for ongoing damage to or decreased functioning of retinal cells.

In some embodiments of the retinal IDM invention described herein, the amplitudes of the corneal ROC changes from CPV-IDM treatment diminish over time. In some embodiments of the retinal IDM invention described herein, the CPV-IDM treatment can be modified by changing the treatment pattern and/or treatment energy density delivered to the cornea in order to make the CPV-IDM changes of corneal ROC temporary for different periods of time. Temporary CPV-IDM-induced ROC changes are particularly useful for treatment of amblyopia in children, adolescents and young adults. CPV-IDM treatment of both eyes of a subject with amblyopia can prevent vision impairment produced by conventional amblyopia treatment with monocular deprivation. CPV-IDM treatment of both eyes of a subject with amblyopia can improve binocularity during normal daily functions, in contrast to conventional single eye methods. Binocularity is impeded by monocular deprivation treatment for amblyopia and is not improved during normal daily functions when conventional binocular visual training is performed with or without video games. CPV-IDM treatment of both eyes of a subject does not prevent use of both eyes' peripheral vision. The peripheral vision of a subject with amblyopia usually is normal, can be impaired by occlusion therapy, and can contribute to improvements in central vision in the amblyopic eye after CPV-IDM treatment.

Figure 13:
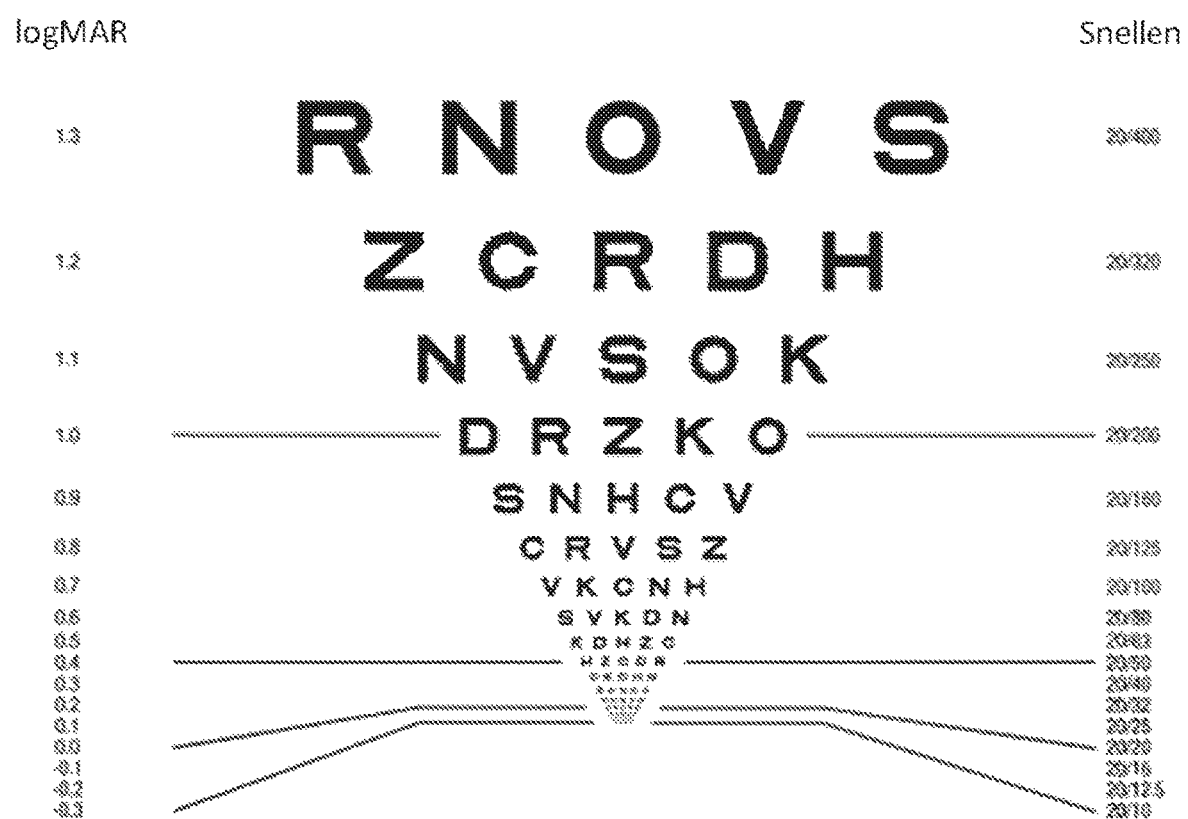
FIG. 13 shows an ETDRS visual acuity chart with lines labelled in logMAR (left) and Snellen (right) units. Each line on the chart has five letters; changes in visual acuity are often given in terms of the letters gained or lost.

In an application of the highly preferred embodiment of the retinal IDM device, CPV-IDM treatments on eyes with age-related macular degeneration (AMD) using a treatment pattern similar to that of FIG. 11A produced significant retinal IDM vision improvements in mean best-spectacle corrected distance and near visual acuities (CDVA and CNVA), in contrast sensitivity and other visual functions, and in vision-related quality of life. FIG. 13 shows an ETDRS visual acuity chart that is used to measure visual acuity. Distance and near versions of the ETDRS chart are available to measure distance and near visual acuities, respectively. ETDRS measurements are reported in several ways: in terms of Snellen values, logMAR values, decimal values and/or the number of letters correctly read (starting with 0 letters for a Snellen value of 20/1000). Improvements in visual acuity are often reported in terms of letters gained and/or lines gained on the ETDRS chart; there are 5 letters per line on the chart.

Figure 14:
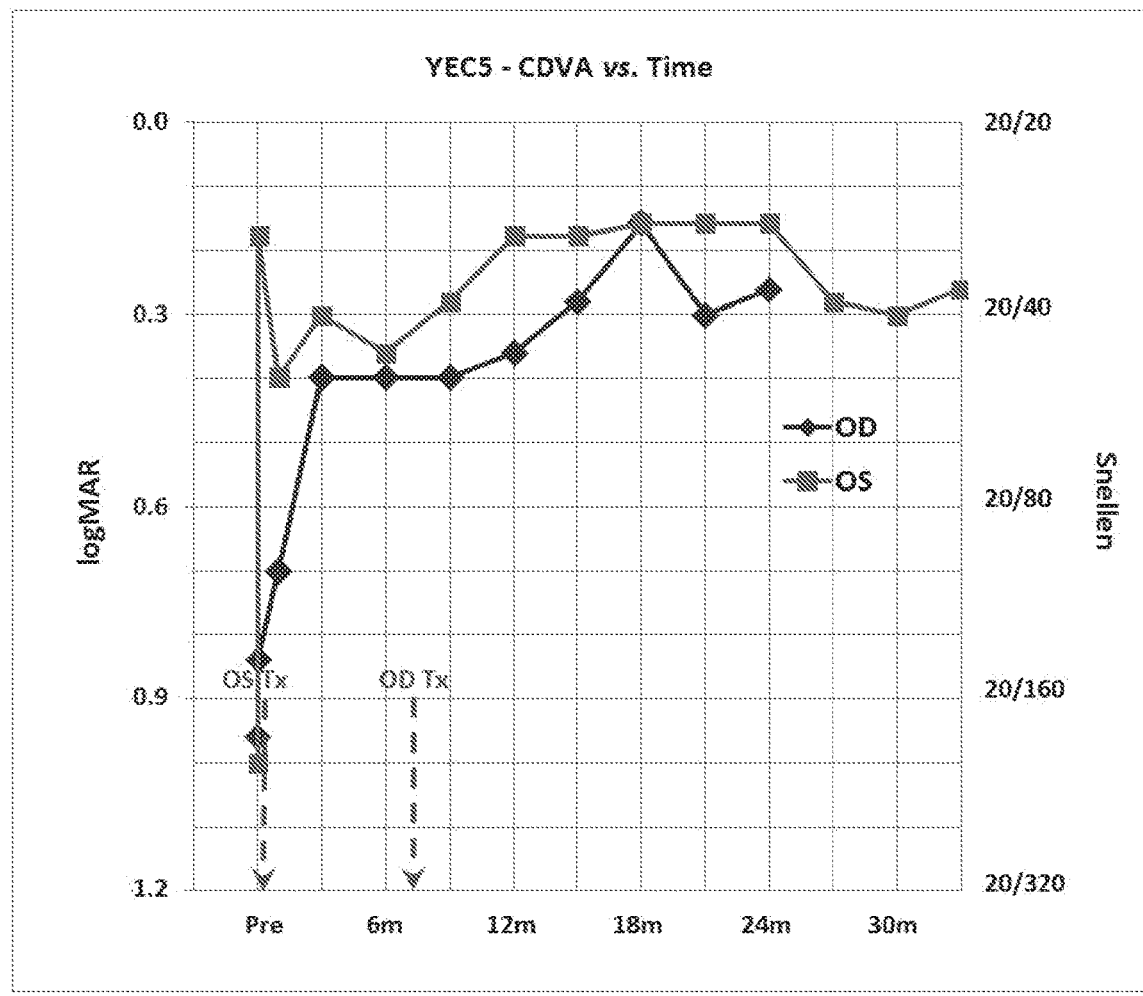
FIG. 14 shows measurements of best spectacle-corrected distance visual acuity (CDVA) vs. time for right (OD) and left (OS) eyes of Patient A. The ordinate grid is shown in both logMAR and Snellen units. The abscissa grid is shown in 3 month increments.
Figure 15:
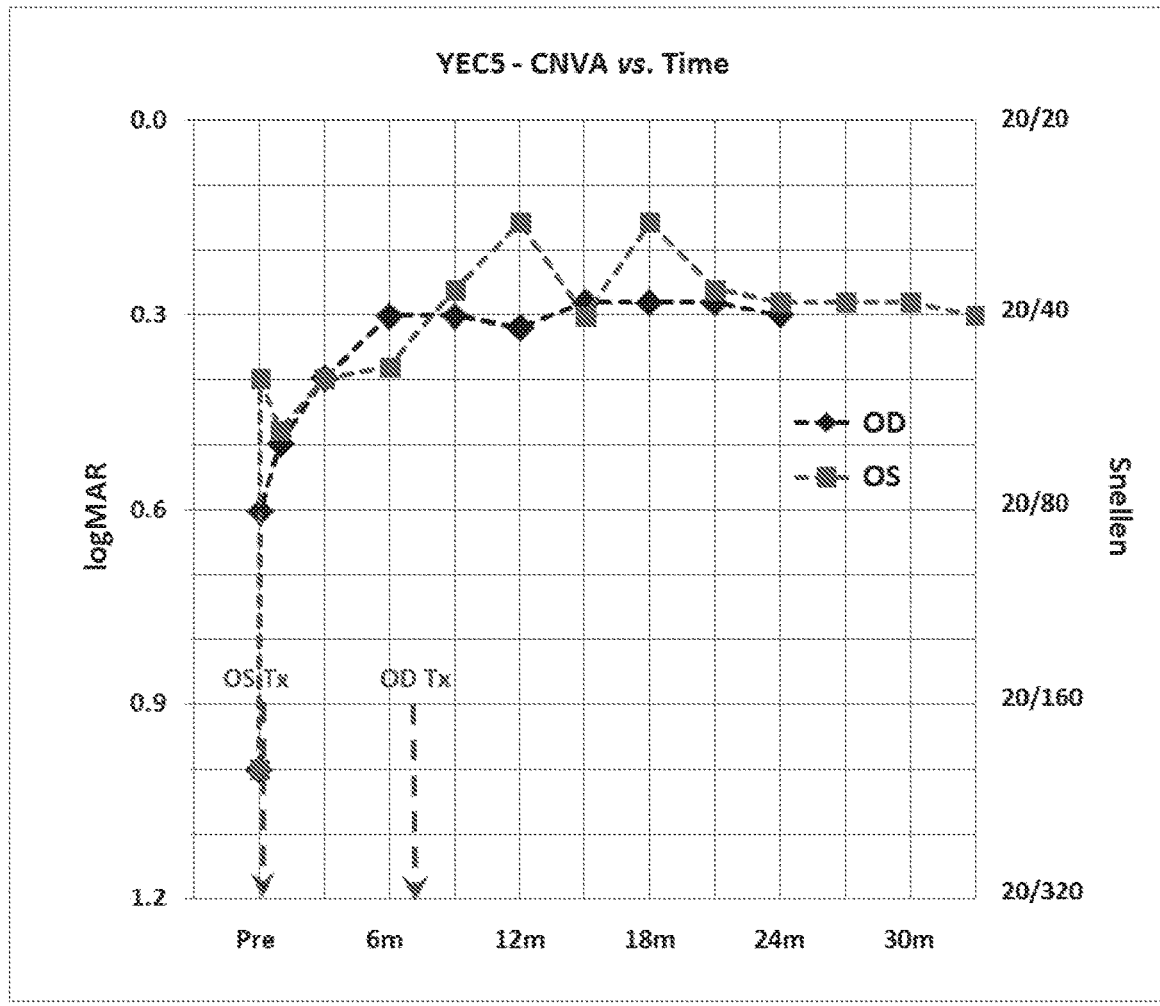
FIG. 15 shows measurements of best spectacle-corrected near visual acuity (CNVA) vs. time for right (D) and left (OS) eyes of Patient A. The ordinate grid is shown in both logMAR and Snellen units. The abscissa grid is shown in 3 month increments.

In one case study, Patient A (a female patient 82 years old with dry AMD in both eyes) received CPV-IDM treatments—initially in her left eye (OS) and, 7.2 months later, in her right eye (OD). FIGS. 14 and 15 show Patient A measured CDVA and CNVA values, respectively, as a function of time. Before treatment of OS, Patient A's best spectacle-corrected distance visual acuities (CDVAs) were 20/182 (OD) and 20/200 (OS), respectively, and her best spectacle-corrected near visual acuities (CNVAs) were 20/200 (both OD and OS), all in Snellen notation. FIG. 14 shows that at 1 day (1 d) after CPV-IDM treatment, Patient A CDVAs were 20/138 (OD) and 20/30 (OS), representing 1.2 lines (6 letters) and 8.2 lines (41 letters) gain, respectively, on an ETDRS distance visual acuity chart. FIG. 15 shows that at 1 day (1 d) after CPV-IDM treatment, Patient A CNVAs were 20/80 (OD) and 20/50 (OS), representing 4.0 lines (20 letters) and 6.0 lines (30 letters) gain, respectively, on an ETDRS near visual acuity chart. For Patient A, both CDVA and CNVA continued to improve further at most CPV post-treatment times extending to 33 months (33 m) for OS and 24 m for OD. These gains are significantly superior to those obtained by conventional devices and methods used to treat AMD eyes. A conventional implantable miniature telescope (IMT) study in a controlled clinical trial for similar AMD patients yielded a mean CDVA gain of only 16 letters at 24 m after implantation. In real-life (as contrasted with controlled clinical trial conditions), conventional devices and methods yield even poorer CDVA and CNVA outcomes.

Figure 16:
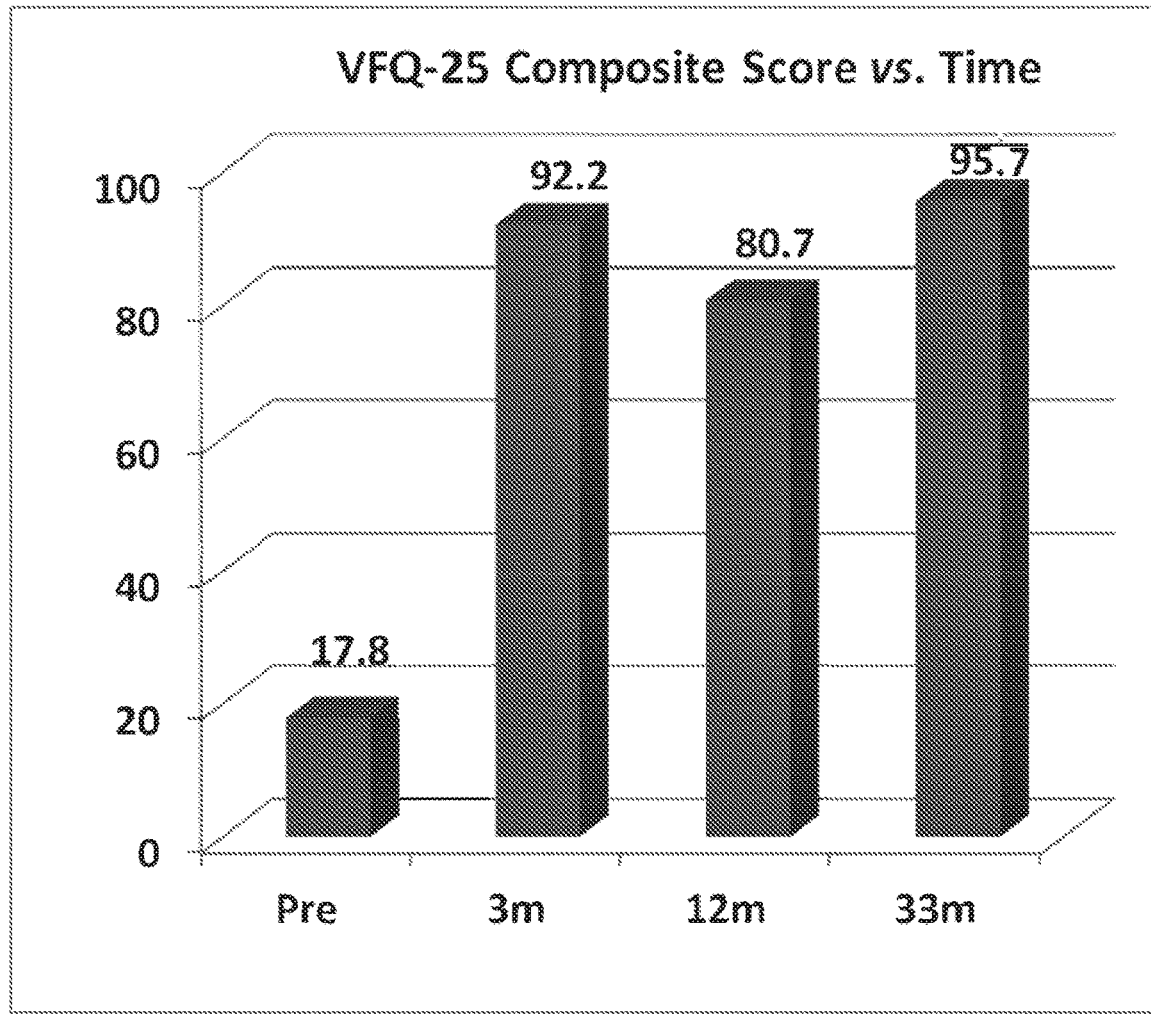
FIG. 16 shows the vision-related quality of life VFQ-25 composite score for Patient A pre- and post-CPV IDM treatment.
Figure 17:
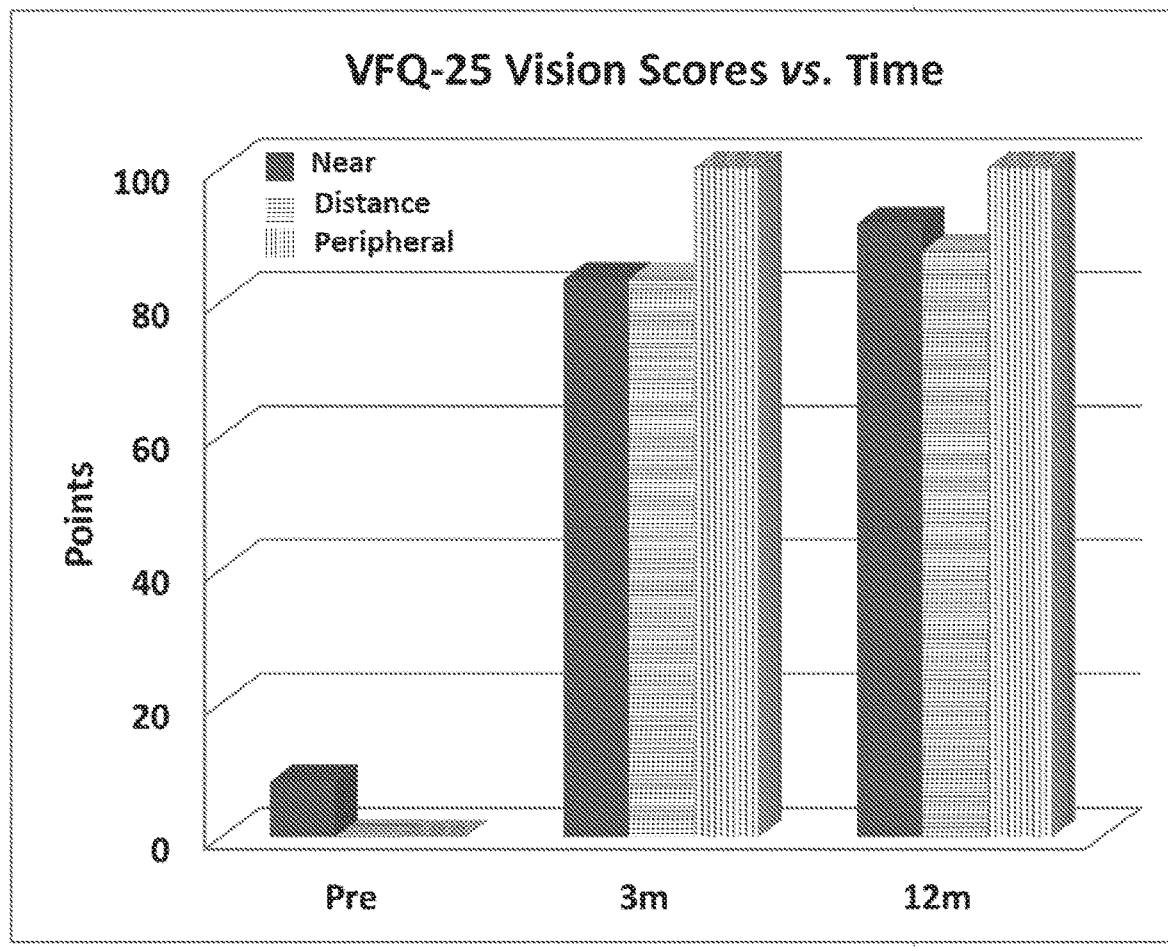
FIG. 17 shows VFQ-25 vision scores for Patient A pre- and post-CPV IDM treatment.
Figure 18:
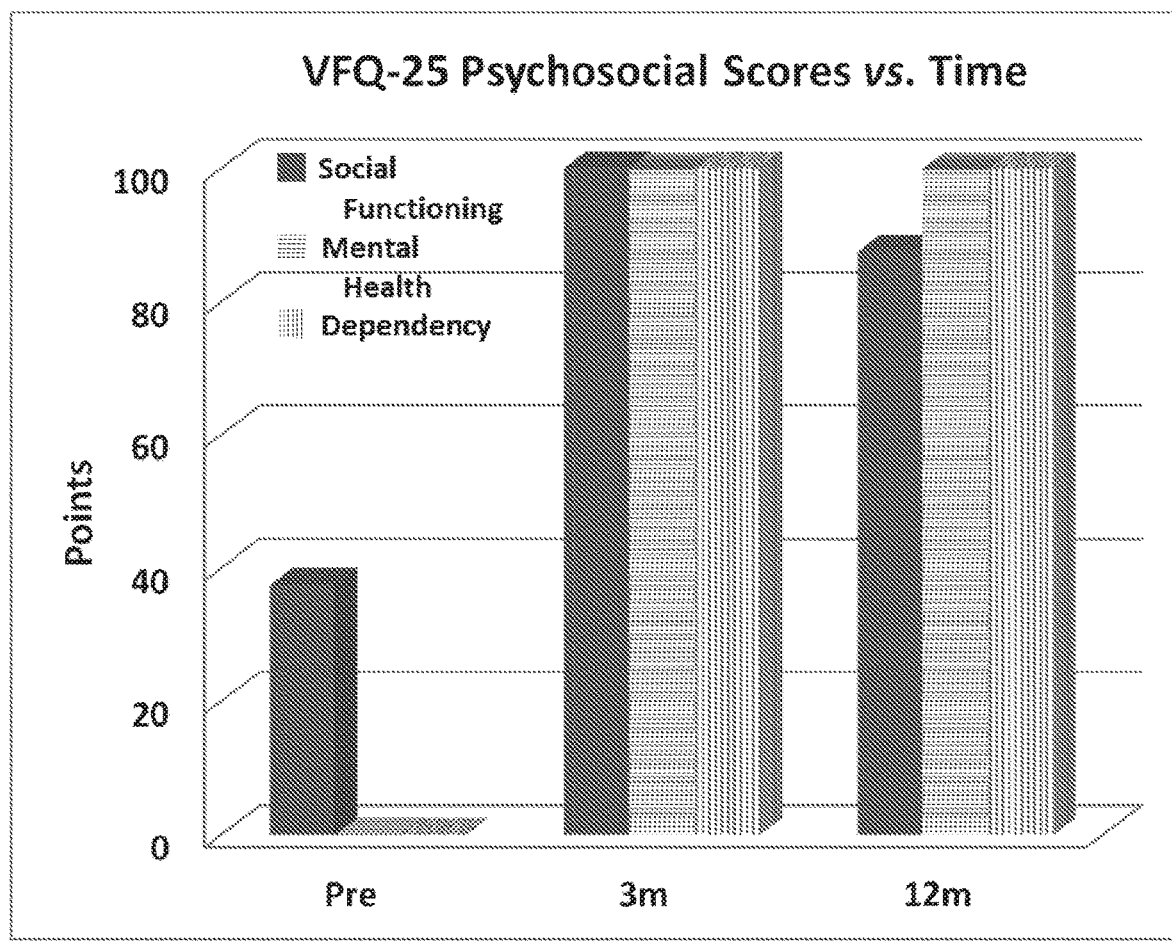
FIG. 18 shows VFQ-25 psychosocial scores for Patient A pre- and post-CPV IDM treatment.

Application of the highly preferred embodiment of the retinal IDM device also yielded significantly better outcomes than conventional devices and methods for many other safety and efficacy measures including, but not limited to, serious adverse events, vision-related quality of life (VRQoL) and visual functions including, but not limited to, contrast sensitivity. With respect to safety, CPV-IDM treatment has not caused to date any CPV-IDM-related adverse event or complication in patients with dry AMD eyes, in contrast to IMT that has substantial percentages of serious adverse events. With respect to VRQoL, FIG. 16 shows the Visual Function Questionnaire-25 (VFQ-25) composite score vs. time for Patient A. The composite score in FIG. 16 is an average of 24 scores (each on a 100-point scale; one score for general health is usually omitted) for responses to items on the VFQ-25 test. Patient A experienced a very large increase in vision-related quality life due to CPV-IDM treatment, as measured by the VFQ-25 composite score. Patient A also experienced very large increases in component vision scores (for near, distance and peripheral vision) shown in FIG. 17 and in component psychosocial scores (for social functioning, mental health and dependency) shown in FIG. 18. With respect to contrast sensitivity (CS), Patient A also experienced a very large increase in CS, as measured on a Pelli-Robson CS chart, from 0.6 log units pre-CPV-IDM treatment to 1.05 log units (for OD, OS and binocular) at 33 months post-CPV-IDM treatment; this log increase represents an increase to 2.8× the pre-treatment value.

Figure 19:
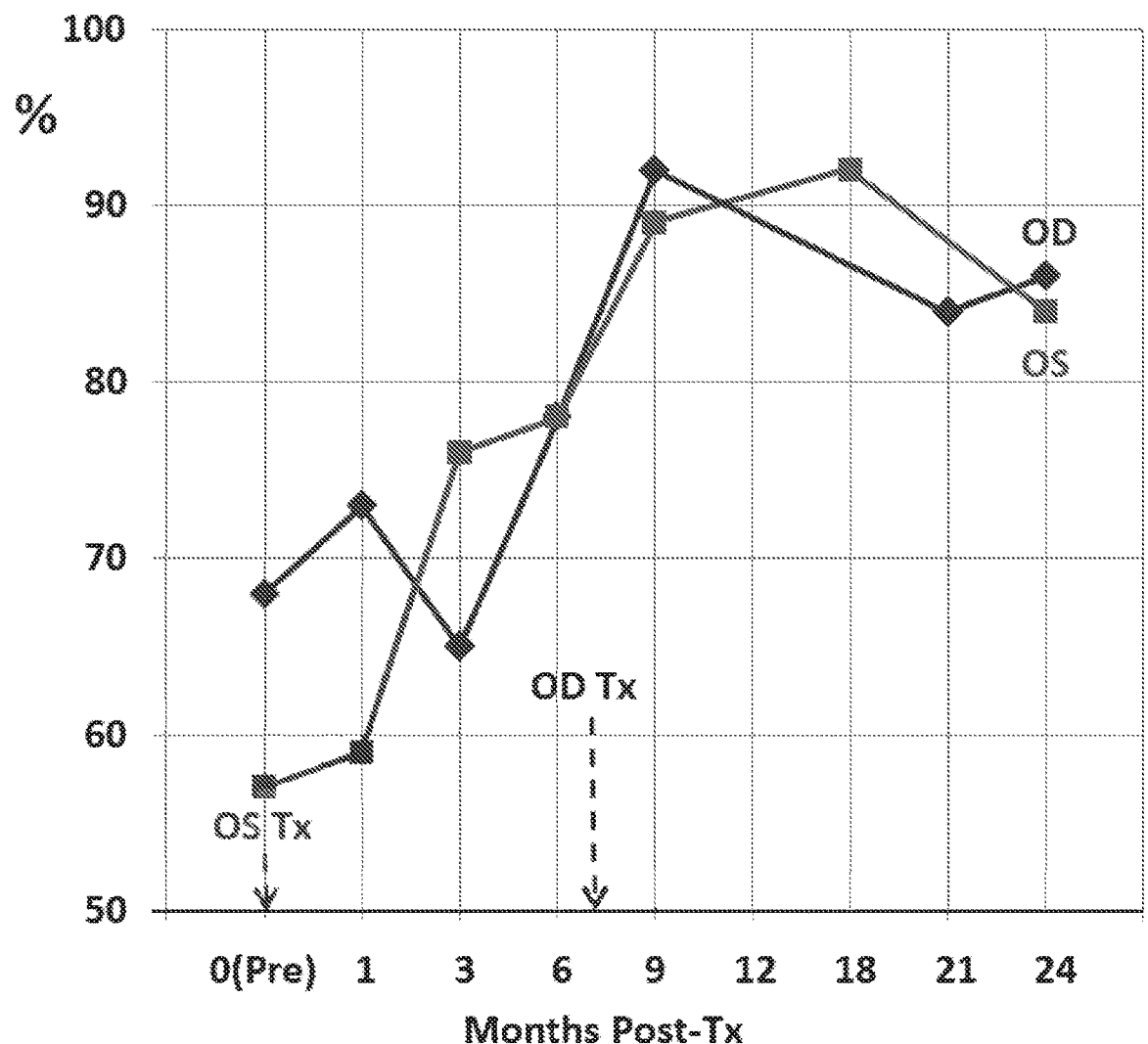
FIG. 19 shows retinal sensitivity measures for Patient A pre- and post-CPV IDM treatment.

Application of the highly preferred embodiment of the retinal IDM device also produced a very significant retinal sensitivity improvement for Patient A. FIG. 19 shows a graph of Patient A outcomes of retinal sensitivity measured in microperimeter examinations as a function of time from pre-CPV-IDM treatment through 24 m post-treatment of OS, the initially treated eye. Retinal sensitivity is graphed as the percentage of stimulus points in the microperimeter grid (of 37 points distributed over a 10° diameter region centered on the fovea) that have retinal sensitivity ≥5 decibels (dB). For OS, the initial treated eye, the number of stimulus points with retinal sensitivity ≥5 dB increased from 21 (57%) pre-CPV-IDM treatment to a maximum of 34 (92%) at 18 m post-treatment and a final value of 31 (84%) at 24 m. Similarly, for OD, the eye treated at 7.2 months after OS treatment, the number of stimulus points with retinal sensitivity ≥5 dB increased from 25 (68%) pre-CPV-IDM treatment to a maximum of 34 (92%) at 9 m post-treatment (with respect to the original OS treatment date) and a final value of 32 (86%) at 24 m (also with respect to the original OS treatment date). As the microperimeter grid of 37 stimulus points is registered on the same points throughout measurements at each time, the increase of retinal sensitivity indicates that CPV-IDM-treatment has provided restorative benefits (i.e., converting some partly or fully dysfunctional regions of the retina into partly or fully functional regions.) Therefore, CPV-IDM treatment may provide a partial cure of AMD in some cases by restorative mechanisms including, but not limited to, beneficial modulation of retinal trophic factors and retinal regeneration of functional retinal cells.

Figure 20:
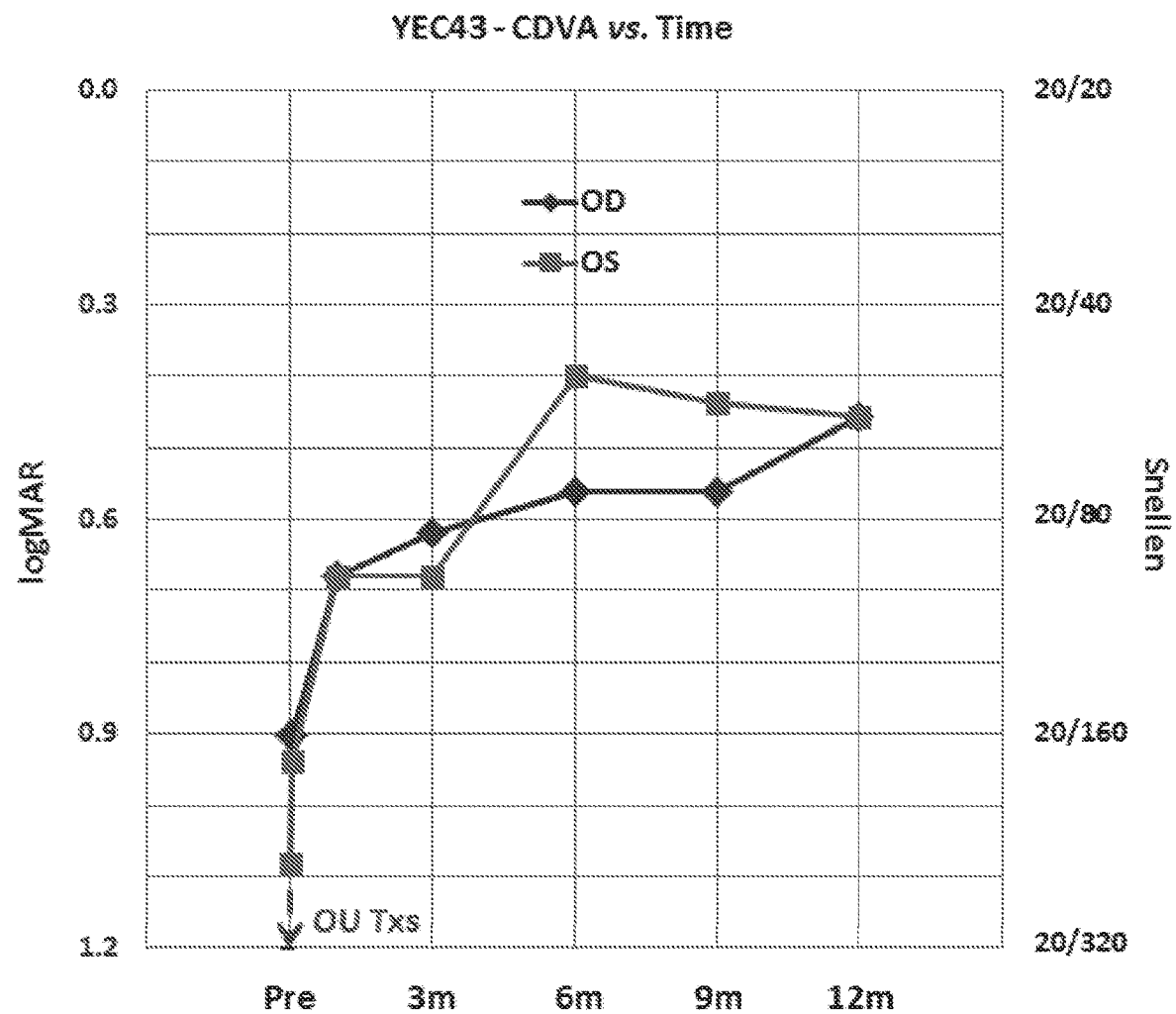
FIG. 20 shows measurements of best spectacle-corrected distance visual acuity (CDVA) vs. time for right (OD) and left (OS) eyes of Patient B. The ordinate grid is shown in both logMAR and Snellen units. The abscissa grid is shown in 3 month increments.
Figure 21:
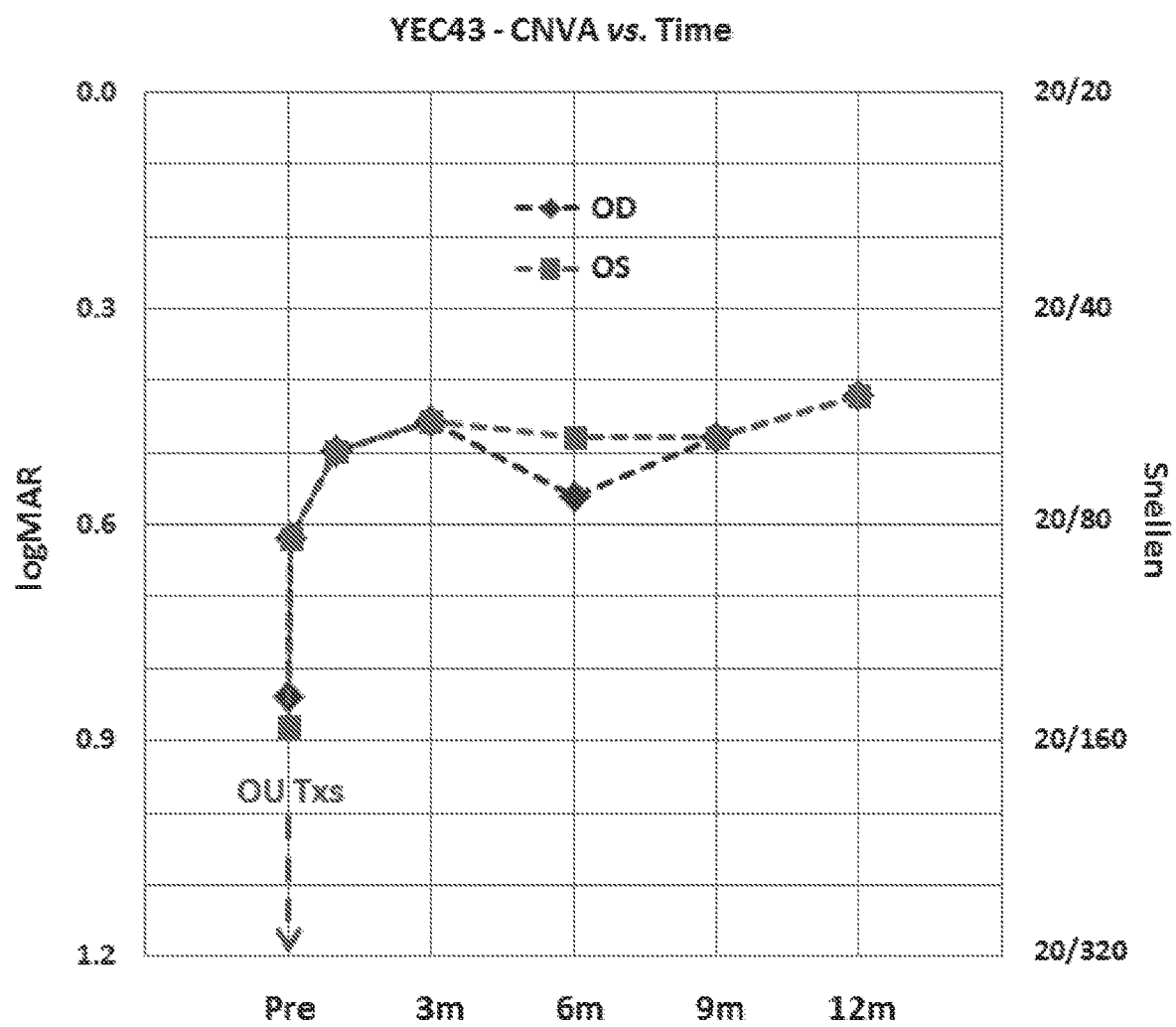
FIG. 21 shows measurements of best spectacle-corrected near visual acuity (CNVA) vs. time for right (D) and left (OS) eyes of Patient B. The ordinate grid is shown in both logMAR and Snellen units. The abscissa grid is shown in 3 month increments.

In another case study, Patient B (a male patient 73 years old with wet AMD in both eyes who is receiving intravitreal injections of anti-VEGF drugs to reduce progression of vision loss) received CPV-IDM treatments in both eyes during a single treatment session. FIGS. 20 and 21 show Patient B measured CDVA and CNVA values, respectively, as a function of time. Before treatment, Patient B's best spectacle-corrected distance visual acuities (CDVAs) were 20/160 (OD) and 20/241 (OS), respectively, and his best spectacle-corrected near visual acuities (CNVAs) were 20/138 (OD) and 20/152 (OS), all in Snellen notation. FIG. 20 shows that at 1 day (1 d) after CPV-IDM treatment, Patient B CDVAs were 20/160 (OD) and 20/174 (OS), representing 0 lines (0 letters) and 1.4 lines (7 letters) gain, respectively, on an ETDRS distance visual acuity chart. At 1 month after CPV-IDM treatment, Patient B CDVAs were 20/96 OU, representing 2.2 lines (11 letters) and 4.0 lines (20 letters) gain, respectively. FIG. 21 shows that at 1 day (1 d) after CPV-IDM treatment, Patient B CNVAs were 20/83 (both OD and OS), representing 2.2 lines (11 letters) and 2.6 lines (13 letters) gain, respectively, on an ETDRS near visual acuity chart. At 1 month after CPV-IDM treatment, Patient B CNVAs were 20/63 OU, representing 3.4 lines (17 letters) and 3.8 lines (19 letters) gain, respectively. For Patient B, both CDVA and CNVA continued to improve further extending to 12 months (12 m) post-treatment, with final gains of 4.2 lines (21 letters) or more for all visual acuity measurements. These gains are significantly superior to those obtained by conventional devices and methods used to treat wet AMD eyes. A conventional anti-VEGF injection study in a controlled clinical trial for wet AMD patients yielded a mean CDVA gain of only 7 letters at 12 m after starting monthly injections of an anti-VEGF drug. In real-life (as contrasted with controlled clinical trial conditions), conventional devices and methods yield even poorer CDVA and CNVA outcomes.

Figure 22:
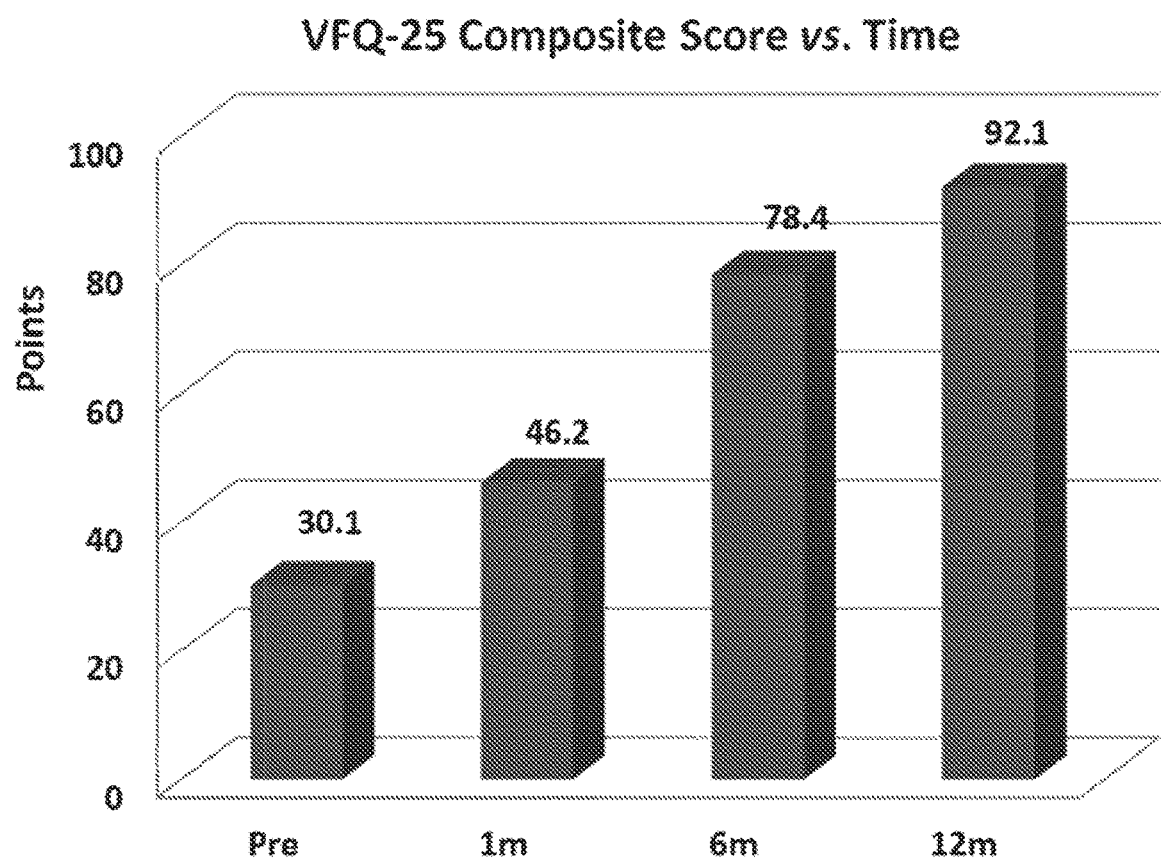
FIG. 22 shows the vision-related quality of life VFQ-25 composite score for Patient B pre- and post-CPV IDM treatment.
Figure 23:
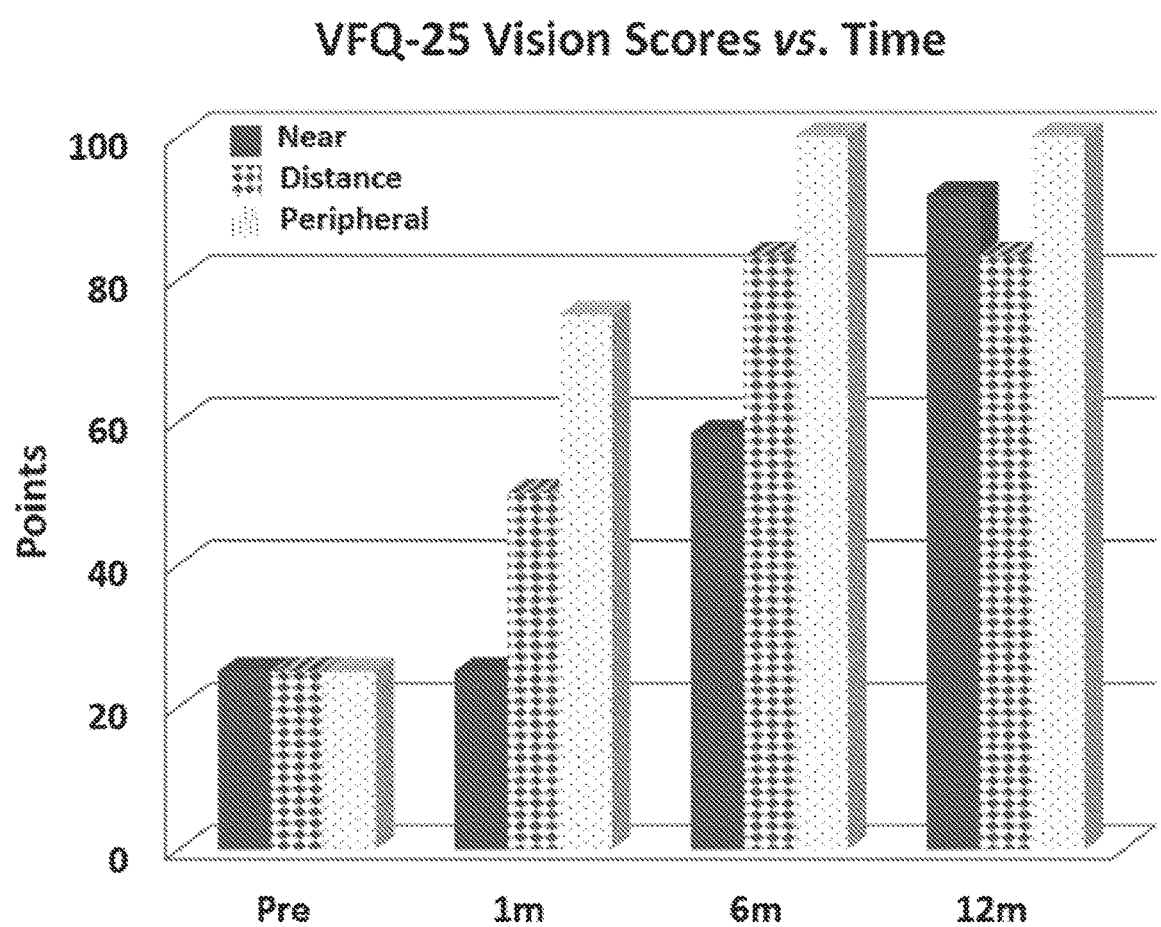
FIG. 23 shows VFQ-25 vision scores for Patient B pre- and post-CPV IDM treatment.
Figure 24:
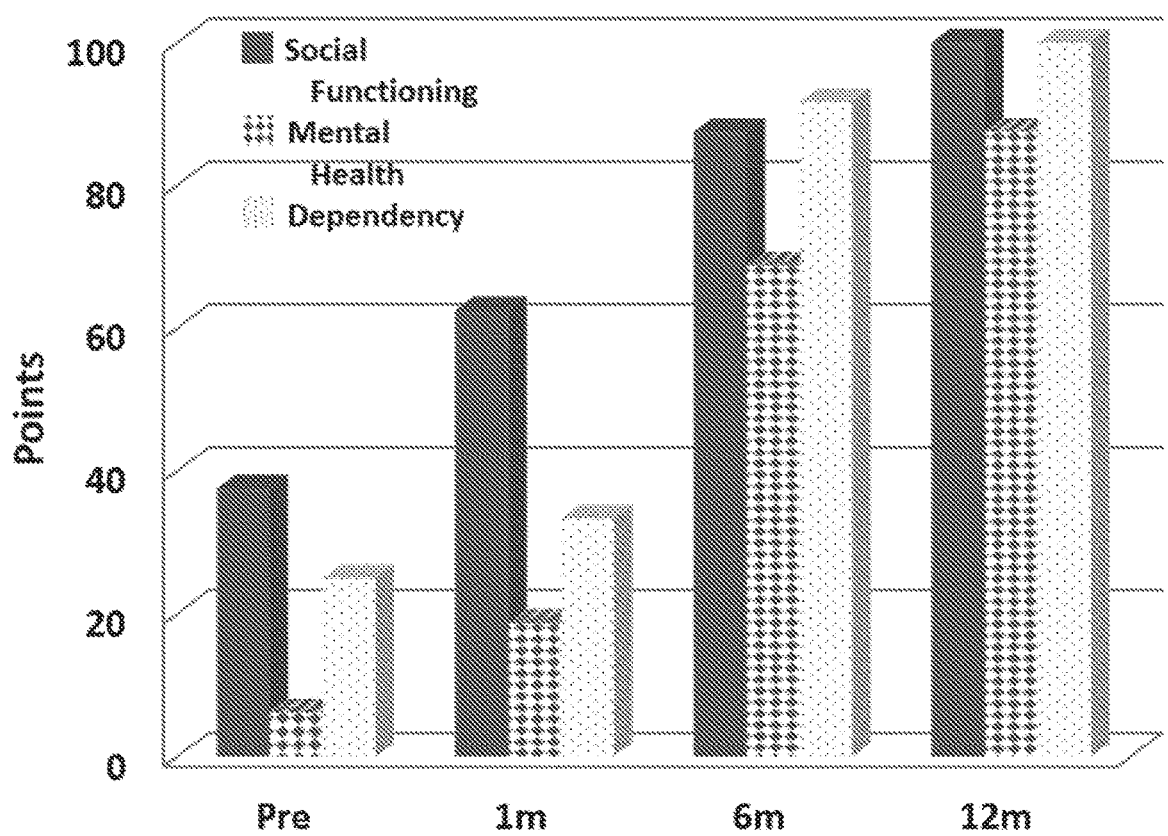
FIG. 24 shows VFQ-25 psychosocial scores for Patient B pre- and post-CPV IDM treatment.

Application of the highly preferred embodiment of the retinal IDM device also yielded significantly better outcomes than conventional devices and methods for many other safety and efficacy measures including, but not limited to, serious adverse events, vision-related quality of life (VRQoL) and visual functions including, but not limited to, contrast sensitivity. With respect to safety, CPV-IDM treatments of patients with wet AMD eyes have not caused any CPV-IMD-related adverse event or complication, in contrast to intravitreal injection anti-VEGF therapies that have substantial percentages of serious adverse events. With respect to VRQoL, FIG. 22 shows the Visual Function Questionnaire-25 (VFQ-25) composite score vs. time for Patient B. The composite score in FIG. 22 is an average of 24 scores (each on a 100-point scale; one score for general health is usually omitted) for responses to items on the VFQ-25 test. Patient B experienced a very large increase in vision-related quality life due to CPV-IDM treatment, as measured by the VFQ-25 composite score. Patient B also experienced very large increases in component vision scores (for near, distance and peripheral vision) shown in FIG. 23 and in component psychosocial scores (for social functioning, mental health and dependency) shown in FIG. 24. With respect to contrast sensitivity (CS), Patient B also experienced a very large increase in CS, as measured on a Pelli-Robson CS chart, from 1.05 log units pre-CPV-IDM treatment to 1.35 log units (for OD, OS and binocular) at 12 months post-CPV-IDM treatment; this log increase represents an increase to 2× the pre-treatment value.

Patient B was diagnosed with wet AMD in both eyes during 2014 and has been receiving anti-VEGF intravitreal injections since then at relatively high frequency—for the 12 months before CPV-IDM treatment, 8 injections OD and 6 injections OS and for the 10 months after CPV-IDM treatment, 8 injections in each eye. Patient B is a combination therapy case in which anti-VEGF injections were, and are continuing to be, used to reduce the neovascularization associated with wet AMD and CPV-IDM treatment was used to improve vision. In some embodiments of the inventions presented herein, combination therapy (involving IDM therapy including, but not limited to CPV-IDM treatment plus another therapy including, but not limited to, pharmacological therapy) produces superior outcomes compared to monotherapy (including, but not limited to, pharmacological therapy).

It can be appreciated by anyone skilled in the art that individual customized retinal IDM treatments can be performed by CPV-IDM for retinal IDM and other devices and methods of the invention described herein. These individual customized retinal IDM treatments can be based on diagnostic information including, but not limited to, individual optical coherence tomography, microperimetry, high definition perimetry and fundus autofluorescence examinations.

In some embodiments of the invention described herein, retinal IDM treatment patterns can be configured based on the extent of macular damage and visual field loss in order to improve vision of patients with glaucoma. Glaucomatous damage to the macula occurs early in the disease process and is more common in the upper visual field where local and deep arcuate defects can appear near fixation. Early glaucomatous damage produces significant reduction in binocular contrast sensitivity scores and depth perception which may be improved by bilateral retinal IDM.

Figure 25:
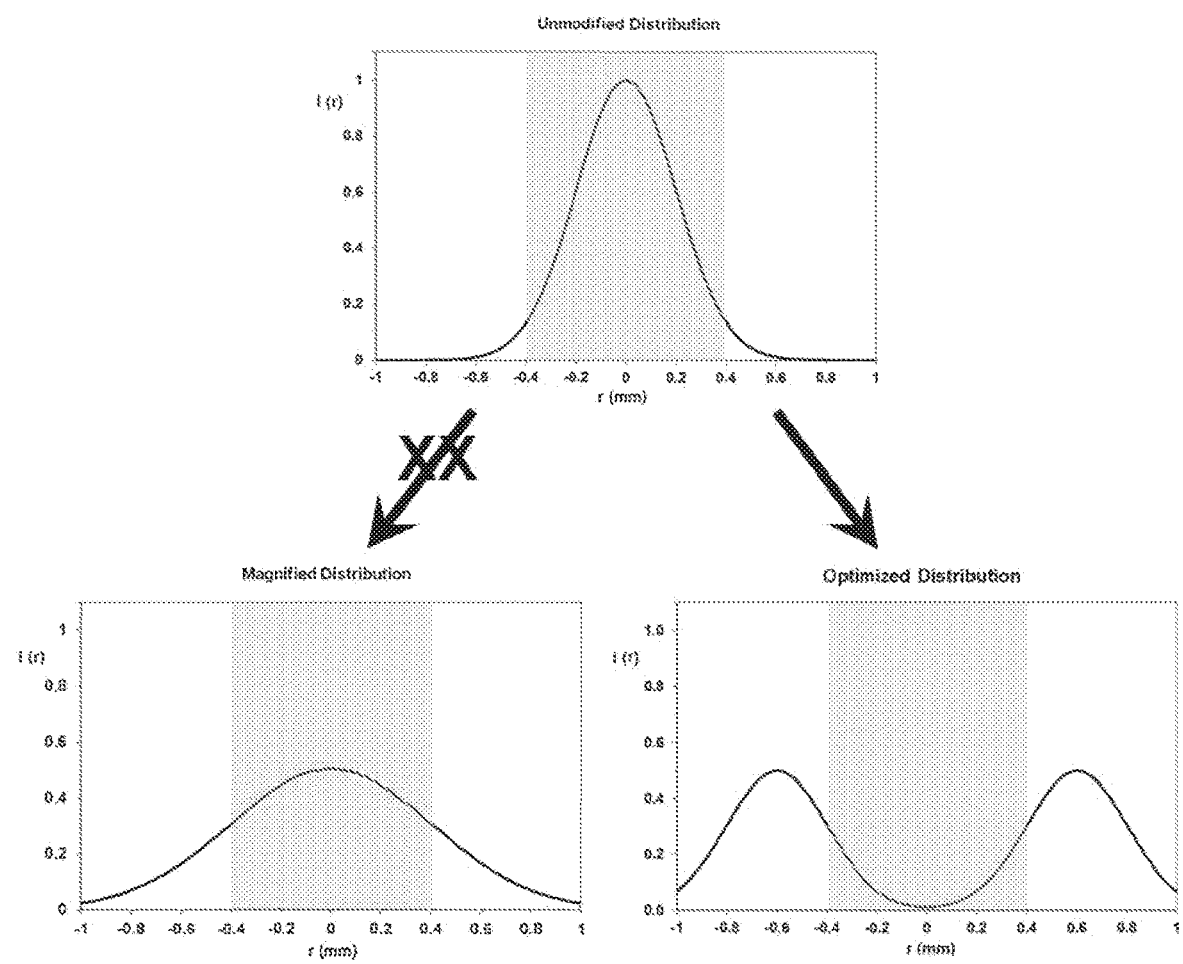
FIG. 25 shows cross-sections through schematic retinal irradiance distributions.

FIG. 25 shows unmodified and modified retinal irradiance distributions with a schematic illustration of the effect of a central dysfunctional retinal area (shaded gray). In the unmodified retinal irradiance distribution (top graph), only a small portion (4.3%) of the light irradiates the functional retinal area that is outside the dysfunctional retinal area. Conventional modification by 2× magnification such as is produced by IMT implantation (bottom left graph) increases the useful retinal irradiance to 30% that is outside the dysfunctional retinal area and inside the functional retinal area. Optimized modification using the invention described herein (bottom right graph) produces retinal IDM similar to that shown in FIG. 7, increasing the useful retinal irradiance to 83% that is outside the dysfunctional retinal area and thus inside the functional retinal area. Conventional modification by magnification, the basis of IMT and similar intraocular telescope devices, is always limited in effectiveness to improve vision for eyes with central vision loss. In addition, the IMT device causes "tunnel vision" due to the restricted field of view of the telescope optics. Corneal treatment by a CPV-IDM device, the preferred embodiment of the invention described herein, is much more effective in improving vision for eyes with central vision loss and also improves peripheral vision rather than causing "tunnel vision".

Some embodiments of the retinal IDM invention described herein involve non-CPV-IDM devices and methods that are configured to produce corneal modifications including, but not limited to, modifications of corneal radii of curvature, corneal indices of refraction, corneal diffraction, corneal scattering and any combination of corneal modifications thereof for light redirections away from the fovea or another retinal fixation region to at least two other retinal regions for retinal IDM. These embodiments include, but are not limited to, corneal devices and methods for corneal photodisruption, corneal photoionization, corneal dissociation, corneal photoablation, photothermal keratoplasty (LTK), corneal photowelding, corneal crosslinking (CXL), conductive keratoplasty (CK), and corneal inlays, all of which are configured for retinal IDM. For optimal retinal IDM, the changes of radii of curvature and/or refractive indices should produce as much retinal IDM as possible outside of dysfunctional retinal areas and inside functional retinal areas. Non-CPV-IDM treatment devices and methods can be configured to produce corneal radii of curvature (ROC) changes including, but not limited to those shown in FIGS. 11 and 12, for corneal anterior surface ROC changes for retinal IDM. IDM treatment and devices can be configured to produce lenticular radii of curvature or indices of refraction modifications of the natural crystalline lens for retinal IDM using devices, including, but not limited, to a femtosecond laser for photodisruption. It is understood that corneal modifications can be made initially (the first modification) and at later times (the subsequent modifications).

Figure 26:
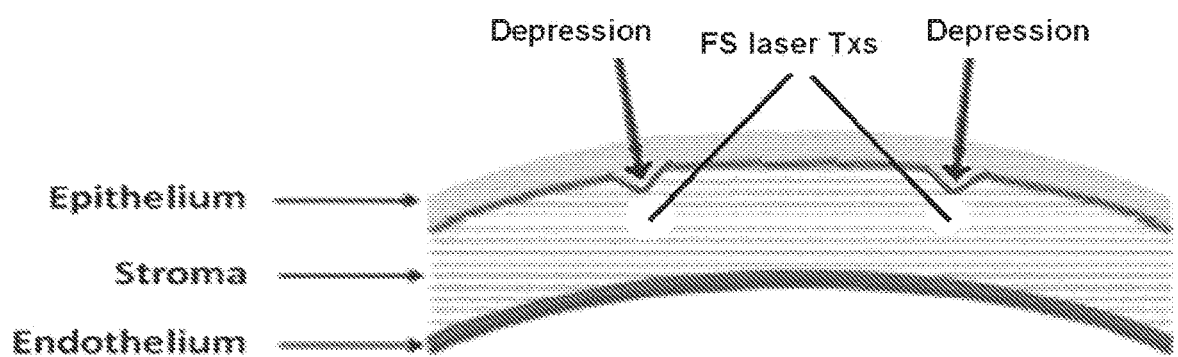
FIG. 26 shows a cross-section of a cornea that has received femtosecond laser treatments to produce corneal anterior surface radius of curvature (ROC) changes for retinal DM.

In some embodiments of the retinal IDM invention described herein, femtosecond (FS) lasers or nanosecond leasers can be used to produce intrastromal photodisruptions or photoionizations or photodissociations or any combination thereof for retinal IDM by means of corneal modifications. FIG. 26 illustrates a schematic cross-section through a cornea that has received a femtosecond (FS) laser treatment (Tx) pattern configured to produce retinal IDM. In the example shown, intrastromal FS laser irradiations are configured to remove intrastromal corneal volumes that lead to depressions (exaggerated in depth in FIG. 26) and, hence, radius of curvature (ROC) changes in the anterior corneal surface; as an alternative, FS laser irradiations can be configured to produce other corneal modifications including, but not limited to, intrastromal index of refraction modification, intrastromal diffraction modification and intrastromal scattering modification for retinal IDM; any combination of corneal modification changes can be used for retinal IDM. FS laser patterns for corneal tissue removal or changes in index of refraction can be spherical as shown in FIG. 26 or can have any volumetric shape. FS treated volumes can be located at any depth within the corneal stroma. Two or more FS treated volumes can be generated centrally (within the 3 mm optical zone), paracentrally (within the 3 to 6 mm optical zone) or peripherally (at >6 mm optical zone), with centration or decentration of the treatment pattern with respect to the pupil centroid or another centration reference. The treated volumes can be equal or unequal in shape and/or depth to produce custom effects. Unlike FS annular intrastromal treatments previously used for other applications such as presbyopia correction, the FS laser modifications of the present invention are not 360 degree annular volumes and, therefore, do not induce corneal ectasia.

In some embodiments of the retinal IDM invention described herein, laser tissue removal procedures including, but not limited to, laser photodisruption, photoionization or photodissociation and/or laser photoablation devices and methods [including, but not limited to, Small Incision Lenticule Extraction (SMILE), Laser In-Situ Keratomileusis (LASIK) and PhotoRefractive Keratectomy (PRK) devices and methods] can be used to produce corneal modifications that are useful for retinal IDM. FIG. 12 shows a cross-section through a cornea with an anterior surface ROC profile that is configured to be useful for retinal IDM. Laser tissue removal procedures (including, but not limited to, femtosecond laser treatment to form a corneal lenticule for SMILE treatment, and laser photoablation of the stromal bed for LASIK treatment and for PRK treatment) should be configured to produce corneal modifications that are sufficient to provide retinal IDM.

In some embodiments of the retinal IDM invention described herein, corneal crosslinking devices, including but not limited to ultraviolet A (UVA) light emitting devices, LTK devices, and CPV devices that can be combined with a photosensitizer, including, but not limited to, riboflavin, or other photoactivation systems with photoactivation agents, including, but not limited to, glyceraldehyde, glutaraldehyde, genipin, nitroalcohols or formaldehyde-releasing agents, for corneal crosslinking (CXL) procedures are configured to produce focal areas of crosslinking (FCXL) In some embodiments of a FCXL IDM procedure, corneal areas that are not to be treated are masked from UVA light or other light or photoactivator in two or more spatially separated treatment areas of the cornea for the application of retinal IDM. FCXL may be performed with or without removal of the corneal epithelium, in whole or in part, to enhance the penetration of a photosensitizer into the corneal stroma, including, but not limited to, administration of a photosensitizer (including, but not limited to, riboflavin) to the cornea followed by UVA or other light irradiation. FXCL can also be produced by using combined laser thermal keratoplasty plus CXL using photosensitizers including, but not limited to, riboflavin that is activated by high irradiance (10 $W/cm^2$ or greater irradiance) visible or UVA light sources including, but not limited to, GaN diode lasers and diode-pumped solid state (DPSS) lasers operating in the 360 to 460 nm wavelength region. FXCL IDM devices and methods are configured to produce corneal modifications including, but not limited to, corneal radius of curvature modifications shown in FIGS. 11 and 12 using various treatment patterns, including but not limited to two or more non-central treatments to induce various locations and amplitudes of corneal modifications for light redirections away from the fovea to two other retinal regions. Within each treatment pattern, FCXL is configured to produce treatment volumes that are at least 0.1 mm in diameter and that are located paracentrally (within the 3 to 6 mm optical zone) or peripherally (at >6 mm optical zone), with centration or decentration of the treatment pattern with respect to the pupil centroid or another centration reference.

In some embodiments of the retinal IDM invention described herein, conventional corneal shape changing procedures and devices including, but not limited to, conductive keratoplasty (CK) and devices, including but not limited to radiofrequency emitting devices, are configured to produce corneal modifications in two or more spatially separated treatment areas of the cornea for retinal IDM. CK-produced corneal modifications include, but are not limited to, corneal radius of curvature modifications shown in FIGS. 11 and 12 using various treatment patterns, including but not limited to two or more non-central treatments to induce various locations and amplitudes of ROC modifications. Within each treatment pattern, CK is configured to produce treatment volumes that are at least 0.1 mm in diameter and that are located paracentrally (within the 3 to 6 mm optical zone) or peripherally (at >6 mm optical zone), with centration or decentration of the treatment pattern with respect to the pupil centroid or another centration reference.

Figure 27:
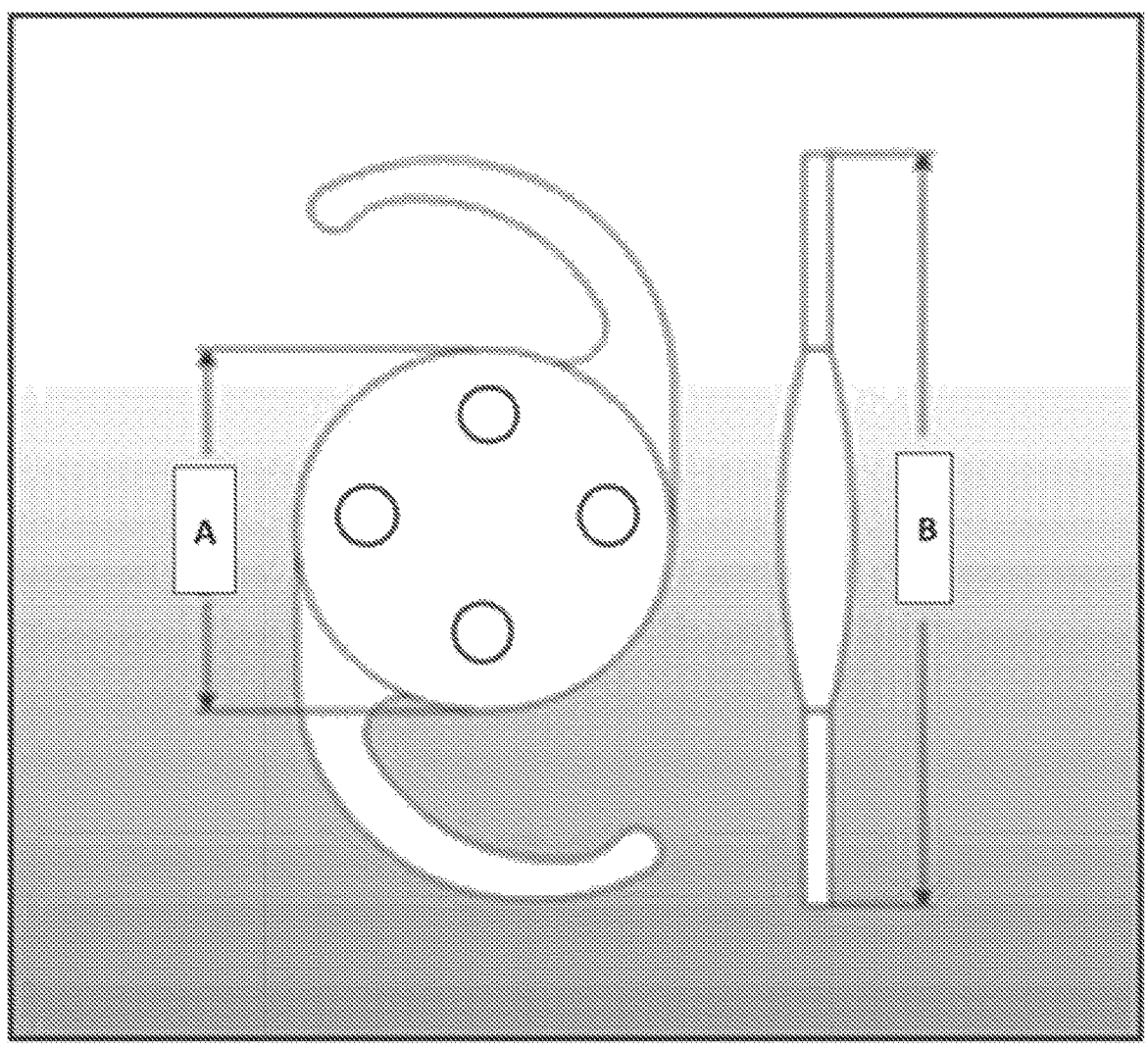
FIG. 27 is an IDM intraocular lens drawing with modifications in paracentral areas.

In some embodiments of the invention described herein, retinal IDM is produced by insertion of an intraocular lens (IOL) and/or an intraocular lens accessory device (IOLAD) configured to modify the retinal IDM. IOLADs include, but are not limited to, light-steering structures including, but not limited to, refractive structures, diffractive structures or any combination thereof that act in combinations with IOLs to modify the retinal IDM. IOLs and IOLADs for phakic, aphakic or pseudophakic eyes include, but not limited to, IOLs and IOLADs positioned in the sulcus or capsular bag, anterior chambers IOLs and IOLADs, iris-fixated IOLs and IOLADs and transscleral-sutured IOLs and IOLADs. FIG. 27 illustrates an IOL modification suitable for retinal IDM that includes four paracentral regions with IOL modifications including, but not limited to, modifications of IOL radii of curvature, IOL indices of refraction, IOL diffraction, IOL scattering and any combination of IOL modifications thereof compared to the other regions of the IOL. In the case of IOL diffraction modifications, the modifications of the invention described herein are different from annular (ring-like patterns centered of the IOL center) modifications that are used in diffractive multifocal IOLs; for example, FIG. 27 illustrates four separate paracentral regions, one or more of which incorporate modifications of IOL diffraction. Additional IOL modifications include, but are not limited to, inclusion of light-steering structures (including, but not limited to, one or more reflectors, one or more optical fibers, one or more prisms or any combination of light-steering structures) within at least one paracentral region of the IOL. It is understood that two, three or more central, paracentral or peripheral regions that are spatially separated, with or without overlapping of the regions, can be used to produce IOL modifications in any or all of the regions for light redirections away from the fovea or another retinal fixation region to two or more retinal regions. It is also understood that IOL and IOLAD modifications can be configured in the IOL and IOLAD before and/or after IOL and IOLAD insertion; after insertion, a FS laser, another light source and/or electronic means can be used to produce IOL and IOLAD modifications in situ in order to produce adjustments to IOL and IOLAD radii of curvature, IOL and IOLAD indices of refraction, IOL and IOLAD light-steering structures, IOL and IOLAD diffraction, IOL and IOLAD scattering and any combination of adjustments thereof.

Figure 28:
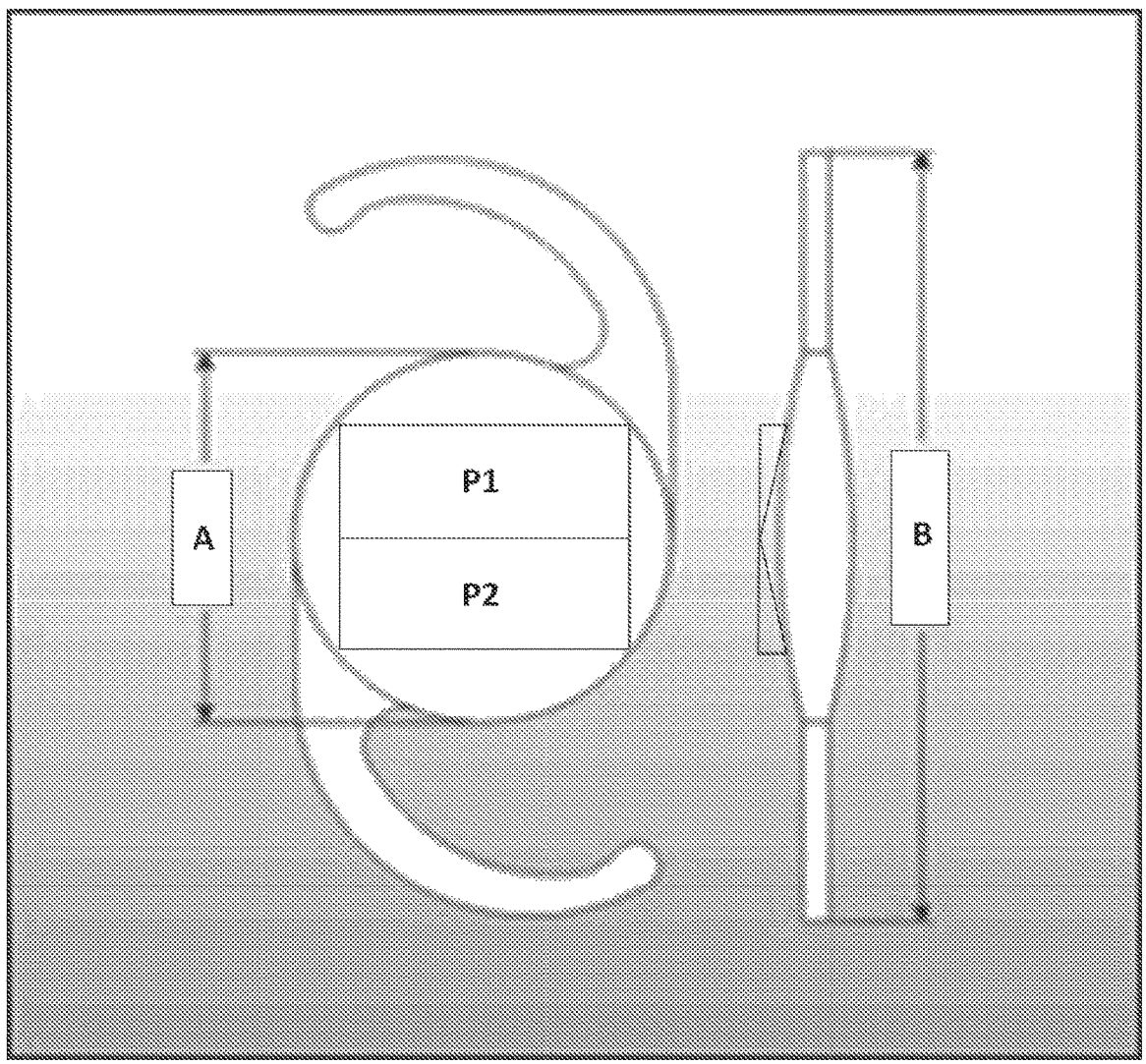
FIG. 28 is an IDM intraocular lens drawing with two prismatic sectors.

FIG. 28 illustrates an IOL modification suitable for retinal IDM that includes two or more prisms that direct irradiance onto functional areas of the retina. In addition, IOLs can be configured to include a combination of at least two central, paracentral or peripheral regions that are spatially separated, with or without overlapping of the regions to modify radii of curvature and/or indices in refraction in any or all of the regions and two or more prisms can be used for retinal IDM. For optimal retinal IDM in eyes with dysfunctional retinal areas, the changes of radii of curvature, changes of refractive indices, prismatic effects, or any combination thereof should produce as much retinal IDM as possible outside of dysfunctional retinal areas and inside functional retinal areas.

Figure 29:
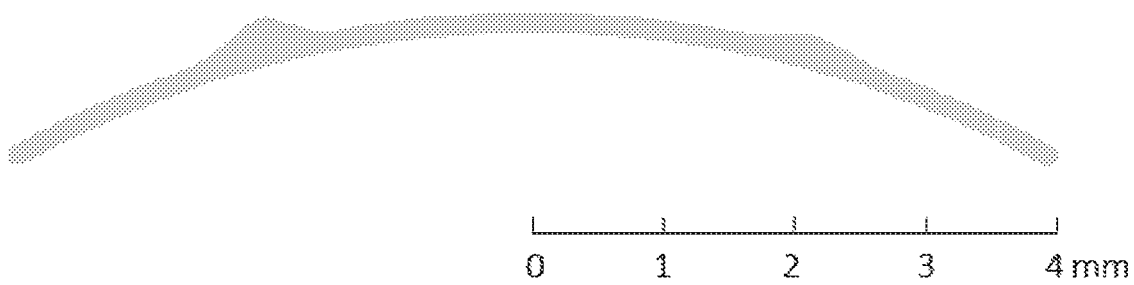
FIG. 29 is a schematic cross-section of an IDM contact lens with paracentral steepened regions.

Some embodiments of the retinal IDM invention described herein involve retinal IDM produced by spectacles, contact lenses or any combination thereof, with modifications including, but not limited to, modifications of radii of curvature, indices of refraction, diffraction, scattering and any combination of modifications thereof for light redirection away from the fovea or another retinal fixation region to at least two other retinal regions that are configured to produce retinal IDM. FIG. 29 shows a cross-section of a modified contact lens (CL; dimensions: 8 mm diameter, 0.2 mm thickness, 7.8 mm anterior and posterior radii of curvature) that includes paracentral steepened regions designed to redirect retinal irradiance from dysfunctional to functional retinal areas. CL dimensions may be different from those shown to include smaller or larger diameters, thicknesses and radii of curvature. Spectacle lenses can also be designed for retinal IDM. Spectacle lenses (SLs) and CLs may be fabricated from a single material or multiple materials. CLs may be corneal, scleral or a combination thereof. Modified SL and CL regions may have different or the same radii of curvature, different or the same refractive indices, different or the same diffraction, different or the same scattering or any combination thereof. Additional spectacle modifications include, but are not limited to, inclusion of light-steering structures including, but not limited to, at least one reflector and at least one optical fiber array within one or both spectacle lenses. There may be 1, 2 or more than 2 modified regions that are located centrally, paracentrally or peripherally within the CL diameter and/or within the SL shape. SLs and CLs may be used in one eye, both eyes or in any SL and CL combination. All SL and CL characteristics, dimensions and modifications are designed to direct light rays into an optimal retinal irradiance distribution for patient retinal IDM requirements. SLs and CLs can be configured statically or actively wherein static configuration is completed prior to incorporation within the ocular system and wherein active configuration is accomplished one or more times after incorporation within the optical system by means of adjustments including, but not limited to, electronic and/or photonic adjustments to corneal radii of curvature changes, indices of refraction changes, diffraction changes, scattering changes and any combination of changes thereof.

Some further embodiments of the retinal IDM invention described herein involve the use of "trial" spectacle lenses (SLs), "trial" contact lenses (CLs), or any combination thereof for screening and/or customization purposes. In the screening application, "trial" lenses may help to determine whether patient eyes are capable of achieving vision and visual function improvements by retinal IDM devices and methods. In the customization application, "trial" lenses may be varied in characteristics to determine the optimal retinal IDM configuration. In both the screening and customization applications, it may be desirable for the patient to use the "trial" lenses for an extended period of days or weeks in order to obtain neuroadaptation benefits.

Figure 30:
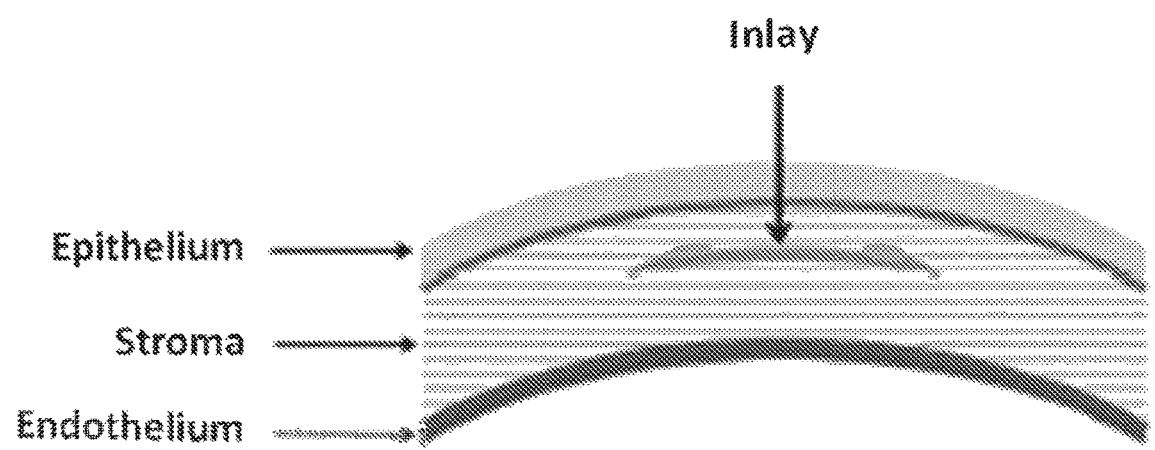
FIG. 30 is a schematic cross-section of an IDM corneal inlay implanted within a cornea.

Some embodiments of the retinal IDM invention described herein involve retinal IDM produced by corneal inlays (CIs). FIG. 30 shows a corneal inlay (CI) that is implanted into the cornea; the corneal segment shown is ca. 1.8 mm long with a central thickness of 0.55 mm but the corneal segment can have lengths extending to ca. 11 mm. Two lenses are shown on the inlay; these lenses can have the same or different modifications including, but not limited to, modifications of radii of curvature, indices of refraction, diffraction, scattering and any combination of modifications thereof. CI shapes can be circular or non-circular. The CI dimensions include, but are not limited to, lengths of 1 to 8 mm, widths of 1 to 8 mm, diameters of 3 to 8 mm and uniform or variable thicknesses in the range of 0.01 to 0.5 mm. There can be one, two, or more inlays, each of which can have 0, 1, 2, or more lenses. The inlay(s) can be located centrally as shown in FIG. 30 or can be located eccentrically. The inlay(s) can be implanted at depths from the anterior corneal surface including, but not limited to, depths of 0.05 to 0.5 mm. The lenses on each corneal inlay can be located on any position on each inlay. CIs are composed of materials including hydrogels, biocompatible materials and other materials known to those skilled in the art. Corneal inlays can be configured statically or actively wherein static configuration is completed prior to implantation within the cornea and wherein active configuration is accomplished one or more times after implantation within the cornea by means of adjustments including, but not limited to, electronic and/or photonic adjustments to corneal radii of curvature changes, indices of refraction changes, diffraction changes, scattering changes and any combination of changes thereof.

In some embodiments of the retinal IDM invention described herein, retinal IDM devices and methods combine retinal IDM teachings with prior art retinal treatments, including pharmacological and/or retinal laser and/or radiation and/or stem cell transplantation and/or epigenetic and/or genetic and/or other therapy (hereafter other therapies) in order to improve treatment of macular degeneration and/or diabetic retinopathy and/or glaucoma and/or other neovascular and/or atrophic and/or inflammatory and/or genetic and/or nutritional and/or age-related retinal diseases (hereinafter "retinal diseases"). The devices and methods of the present invention overcome drawbacks and deficiencies of prior art by introducing different mechanisms of vision and/or retinal pathology and/or repair processes associated with retinal diseases. The devices and methods of the present invention overcome drawbacks and deficiencies of prior art therapies by synergistically combining them with retinal IDM with other therapies to improve visual and/or anatomic outcomes, which also improves patient compliance with prior art therapy. The combination therapy can be administered in the same patient visit or sequentially at different times. In some embodiments of combination therapy, retinal IDM treatment is delivered at one time, either before non-retinal IDM therapy or at some time following initiation of non-retinal IDM therapy. In some embodiments of combination therapy, more than one retinal IDM treatment is delivered at separate times, either before other therapies or at variable times following initiation of non-retinal IDM therapy.

In some embodiments of the retinal IDM invention described herein, retinal IDM treatment is combined with other therapies for retinal diseases, including but not limited to retinal laser therapies, including but not limited to photobiomodulation, laser photocoagulation, laser photodynamic therapy, subthreshold micropulse laser therapy, glaucoma laser therapy, (including, but not limited to, laser trabeculoplasty and cyclophotocoagulation), glaucoma filtration surgery (including, but not limited to, trabeculectomy, microtrabeculectomy, internal or external tube shunt implantation, suprachoroidal shunt implantation), stem cell transplantation, and radiation therapy (including but not limited to focal intraocular strontium 90 beta radiation).

In some embodiments of the retinal IDM devices and methods described herein, retinal IDM treatment is combined with other therapies for retinal diseases including, but not limited to, genetic, epigenetic and optogenetic therapy.

In some embodiments of the retinal IDM invention described herein, retinal IDM treatment is combined with pharmacological treatment of retinal diseases, including pharmacologic agents, including nutritional supplements, administered orally, topically to the cornea, via subconjunctival injection, via intravitreal injection, intraretinally, via implants and via iontophoresis.

In some embodiments of the retinal IDM invention described herein, retinal IDM treatment is combined with antiangiogenesis drug therapy.

In some embodiments of the retinal IDM invention described herein, retinal IDM provides a method of ameliorating or treating an ocular disorder, including but not limited to macular degeneration, choroidal neovascularization or diabetic retinopathy in a subject comprising treatment by retinal IDM in combination with administering a therapeutically effective amount of any vascular endothelial growth factor (VEGF) antagonist including, but not limited to ranibizumab, bevacizumab, brolucizumab and aflibercept, in combination with administering a therapeutically effective amount of any PDGF antagonist including, but not limited to, volociximab and P200, or in combination with any combination of the above drugs. As used herein, the term "ameliorating" or "treating" or "compensating for" means that the clinical signs and/or symptoms associated with an ocular disorder (e.g., macular degeneration) are lessened as result of the actions performed. The signs or symptoms to be monitored will be characteristic of the ocular disorder and will be well known to physicians skilled in the art, as will the methods for monitoring the signs, symptoms and conditions.

In some embodiments of the retinal IDM invention described herein, retinal IDM provides a method of ameliorating or treating an ocular disorder, including but not limited to macular degeneration, choroidal neovascularization or diabetic retinopathy in a subject comprising treatment by retinal IDM in combination with administration of a therapeutically effective amount of vetalanib or pazopanib or any other tyrosine kinase inhibitor or any other inhibitor of phosphorylation of VEGF and PDGF receptors.

In some embodiments of the retinal IDM invention described herein, retinal IDM provides a method of treating an ocular disease in a subject comprising treatment by retinal IDM in combination with administering a therapeutically effective amount of an inhibitor of VEGF activity.

In some embodiments of the retinal IDM invention described herein, retinal IDM provides a method of treating or ameliorating an ocular disease in a subject comprising treatment by retinal IDM in combination with administering a therapeutically effective amount of an inhibitor of alpha5beta1 integrin activity.

In some embodiments of the retinal IDM invention described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of PDGF activity.

In some embodiments of the retinal IDM invention described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of tyrosine kinase activity.

In some embodiments of the retinal IDM invention described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of an inhibitor of mTOR (sirolimus).

In some embodiments of the retinal IDM invention described herein, retinal IDM provides a method of treating or ameliorating an ocular disease, including but not limited to a neovascular ocular disease and/or wet macular degeneration, and/or diabetic retinopathy, in a subject comprising treatment by retinal IDM in combination with administering a therapeutically effective amount of fluocinolone acetonide or any other anti-inflammatory agent, wherein the anti-inflammatory agent is delivered by intravitreal injection or delivered by an intraocular implant.

In some embodiments of the retinal IDM invention described herein, retinal IDM provides a method of treating or ameliorating an ocular disease, including but not limited to geographic atrophy and/or dry macular degeneration, in a subject comprising treatment by retinal IDM in combination with administrating a therapeutically effective amount of an inhibitor of complement, including but not limited to complement 3 or 5, activity.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of avacincaptad pegol, LEG316, POT-4, eculizumab, JPE-1375, ARC1905 or any other complement inhibitor.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of doxycycline.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of glatiramer acetate or other T helper 2 inducer or immunomodulator.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of OT551, or any other downregulator of overexpression of the protein complex nuclear factor (NF)¬B or any other antioxidant, or combination of antioxidants, including but not limited to combinations of vitamin C, vitamin E, beta-carotene or lutein and zeaxanthin, and omega-3 fatty acids as in for, example, the Age-Related Eye Disease Study (AREDS) and AREDS 2 studies.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount nicotinamide adenine dinucleotide (NAD) or any precursors of NAD, including but not limited nicotinamide riboside or nicotinamide mononucleotide.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of a trophic factor including, but not limited to, pigment epithelium-derived factor (PEDF), fibroblast growth factors (FGFs) and lens epithelium-derived growth factor (LEDGF).

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of ciliary neurotrophic factor (CNTF) or any other neurotrophic factors or any other inhibitors of photoreceptor apoptosis.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of a neuroprotective agent, including but not limited to brimodinine.

In some embodiments of the retinal IDM invention described herein, retinal IDM provides a method of treating or ameliorating an ocular disease, including but not limited to geographic atrophy and/or dry macular degeneration in a subject comprising treatment by retinal IDM in combination with administering a therapeutically effective amount of a Fas inhibitor or other agent designed to protect retinal cells from cell death.

In some embodiments of the retinal IDM invention described herein, retinal IDM provides a method of treating or ameliorating an ocular disease, including but not limited to geographic atrophy and/or dry macular degeneration and/or neovascular macular degeneration and/or glaucoma in a subject comprising treatment by retinal IDM in combination with administering a therapeutically effective amount of a statin, including but not limited to atorvastin, lovastation, rosuvastatin, fluvastatin or simvastatin.

In some embodiments of the retinal IDM invention described herein, retinal IDM provides a method of treating or ameliorating an ocular disease, including but not limited to glaucoma or ocular hypertension in a subject comprising treatment by retinal IDM in combination with administering a therapeutically effective amount of an intraocular pressure (IOP)—lowering agent, including but not limited to a miotic, an alpha or alpha/beta adrenergic agonist, a beta-blocker, a Ca2+ channel blocker, a carbonic anhydrase inhibitor, chlolinesterase inhibitor, a prostaglandin agonist, a prostaglandin, a prostamide, a cannabinoid, and combinations thereof.

In some embodiments of the retinal IDM invention described herein, retinal IDM provides a method of treating or ameliorating an ocular disease, including but not limited to glaucoma in a subject comprising treatment by retinal IDM in combination with administering a therapeutically effective amount of a pharmacological agent decreasing retinal ganglion cell dysfunction and/or pathology, related to ischemia or excitotoxicity.

In some embodiments of the retinal IDM invention described herein, retinal IDM provides a method of treating or ameliorating an ocular disease, including but not limited to glaucoma in a subject comprising treatment by retinal IDM in combination with administering a therapeutically effective amount of a pharmacological agent decreasing excessive excitatory amino acid (EAA) stimulation (EAA permits the bipolar and amacrine cells to communicate with the ganglion cell), including but not limited to a glutamate antagonist and/or any combination of a glutamate antagonist and at least one IOL-lowering agent.

In some embodiments of the retinal IDM invention described herein, retinal IDM provides a method of treating or ameliorating an ocular disease, including but not limited to glaucoma in a subject comprising treatment by retinal IDM in combination with administering a therapeutically effective amount of a pharmacological agent providing neuroprotection and/or neuroregeneration of retinal ganglion cells, including but not limited to a rho-kinase (ROCK) inhibitor or an adenosine receptor agonist.

What is claimed:

1. An apparatus for improving or restoring vision of an eye having a preferred retinal locus of fixation, the apparatus comprising one or more components configured to be positioned anterior to a retina of the eye and to redirect environmental light within an ocular field of view away from the preferred retinal locus of fixation of the eye to a plurality of retinal locations that are not the preferred retinal locus of fixation, and the apparatus not producing corneal vitrification.

2. The apparatus of claim 1, further comprising a component configured to determine the preferred retinal locus of fixation of the eye.

3. The apparatus of claim 1, further comprising at least one of a refractive component or a diffractive component.

4. The apparatus of claim 1, wherein the apparatus is configured to modify more than one radius of curvature of at least one of the apparatus or a structure within the eye.

5. The apparatus of claim 1, wherein the apparatus is configured to modify more than one index of refraction of at least one of a component of the apparatus or a structure within the eye.

6. The apparatus of claim 1, wherein the apparatus is configured to modify diffraction within at least one of a component of the apparatus or a structure within the eye.

7. The apparatus of claim 1, wherein the plurality of retinal locations to which the environmental light is redirected are disposed within genetically altered portions of the retina.

8. The apparatus of claim 1, wherein the plurality of retinal locations to which the environmental light is redirected are disposed within epigenetically altered portions of the retina.

9. The apparatus of claim 1, wherein the plurality of retinal locations to which the environmental light is redirected are disposed within neuroregeneratively altered portions of the retina.

10. The apparatus of claim 1, wherein the plurality of retinal locations to which the environmental light is redirected are disposed within portions of the retina that includes at least one of a retinal transplant, an implanted retinal cell, an implanted stem cell, or an implanted prosthesis.

11. The apparatus of claim 1, wherein:
the apparatus comprises a lens, the lens configured to be positioned in front of or on the eye and having two or more noncentral, non-annular, and separate modified portions, the two or more noncentral, non-annular, and separate modified portions configured for directing laser light or non-laser ultraviolet light to modify a structure within the eye, the modified structure configured for redirecting environmental light within the ocular field of view away from the preferred retinal locus of fixation of the eye to the plurality of retinal locations that are not the preferred retinal locus of fixation, and the apparatus not producing corneal vitrification; and
a first value of a radius of curvature or an index of refraction of each of the two or more noncentral, non-annular, and separate modified portions of the lens differs from a second value of the radius of curvature or the index of refraction characterizing at least one additional portion of the lens.

12. An apparatus for improving or restoring vision of an eye having a preferred retinal locus of fixation, the apparatus comprising a lens, the lens configured to be positioned in front of or on the eye and having two or more noncentral, non-annular, and separate modified portions, the two or more noncentral, non-annular, and separate modified portions configured for directing laser light or non-laser ultraviolet light to modify a structure within the eye, the modified structure configured for redirecting environmental light within the ocular field of view away from the preferred retinal locus of fixation to a plurality of retinal locations that are not the preferred retinal locus of fixation, and the apparatus not producing corneal vitrification, wherein a first value of a radius of curvature or an index of refraction of each of the two or more noncentral, non-annular, and separate modified portions of the lens differs from a second value of the radius of curvature or the index of refraction characterizing at least one additional portion of the lens.

* * * * *